(12) United States Patent
Nilson et al.

(10) Patent No.: US 7,298,415 B2
(45) Date of Patent: Nov. 20, 2007

(54) STRUCTURED LIGHT IMAGING APPARATUS

(75) Inventors: David Nilson, Walnut Creek, CA (US);
Michael D. Cable, Danville, CA (US);
Bradley W. Rice, Danville, CA (US);
Kevin Kearney, Fairport, NY (US)

(73) Assignee: Xenogen Corporation, Alameda, CA (US)

( * ) Notice: Subject to any disclaimer, the term of this patent is extended or adjusted under 35 U.S.C. 154(b) by 87 days.

(21) Appl. No.: 11/127,842

(22) Filed: May 11, 2005

(65) Prior Publication Data

US 2005/0237423 A1    Oct. 27, 2005

Related U.S. Application Data

(63) Continuation-in-part of application No. 09/905,668, filed on Jul. 13, 2001, now Pat. No. 7,113,217.

(51) Int. Cl.
*H04N 5/222* (2006.01)
*A61B 6/00* (2006.01)

(52) U.S. Cl. ................ 348/370; 600/476
(58) Field of Classification Search ........... 348/207.99, 348/222.1, 370, 373–376, 77; 600/407, 424, 600/476
See application file for complete search history.

(56) References Cited

U.S. PATENT DOCUMENTS

| | | | |
|---|---|---|---|
| 4,687,325 A * | 8/1987 | Corby, Jr. ................ | 356/3.09 |
| 4,687,352 A * | 8/1987 | Igi et al. ................ | 400/73 |
| 4,773,097 A | 9/1988 | Suzaki et al. | |
| 5,202,091 A | 4/1993 | Lisenbee | |
| 5,205,291 A | 4/1993 | Potter | |
| 5,242,441 A | 9/1993 | Avitall | |
| 5,319,209 A | 6/1994 | Miyakawa et al. | |
| 5,334,193 A | 8/1994 | Nardella | |
| 5,414,258 A | 5/1995 | Liang | |
| 5,452,723 A | 9/1995 | Wu et al. | |
| 5,530,652 A * | 6/1996 | Croyle et al. ................ | 700/130 |
| 5,584,872 A | 12/1996 | LaFontaine et al. | |

(Continued)

FOREIGN PATENT DOCUMENTS

EP    1 016 419    7/2000

(Continued)

OTHER PUBLICATIONS

Mahmood et al., "Near-Infrared Optical Imaging of Protease Activity for Tumor Detection," Radiology, Dec. 1999, pp. 866-870.

(Continued)

*Primary Examiner*—Lin Ye
*Assistant Examiner*—Timothy J Henn
(74) *Attorney, Agent, or Firm*—Beyer Weaver LLP

(57) ABSTRACT

The present invention integrates a structured light source into an imaging system for reconstructing surface topography of an object being imaged. The structured light source includes a mechanism for transmitting a set of lines onto the object from an angle. The lines are displaced, or phase shifted relative to a stage, when they encounter an object with finite height, such as a mouse. This phase shift provides structured light information for the object. A camera captures the structured light information. Using software that employs a structured light analysis, surface topography data for the object is determined from the phase shift of the lines.

26 Claims, 19 Drawing Sheets

U.S. PATENT DOCUMENTS

| | | |
|---|---|---|
| 5,594,253 A | 1/1997 | Bueno et al. |
| 5,636,299 A | 6/1997 | Bueno et al. |
| 5,637,874 A | 6/1997 | Honzawa et al. |
| 5,650,135 A | 7/1997 | Contag et al. |
| 5,661,562 A | 8/1997 | Aharon |
| 5,672,881 A | 9/1997 | Striepeke et al. |
| 5,705,807 A | 1/1998 | Throngnumchai et al. |
| 5,738,101 A | 4/1998 | Sappey |
| 5,746,210 A | 5/1998 | Benaron et al. |
| 5,807,262 A | 9/1998 | Papaioannou et al. |
| 5,812,310 A | 9/1998 | Stewart et al. |
| 5,818,587 A | 10/1998 | Devaraj et al. |
| 5,835,617 A | 11/1998 | Ohta et al. |
| 5,840,572 A | 11/1998 | Copeland et al. |
| 5,867,250 A | 2/1999 | Baron |
| 5,953,446 A | 9/1999 | Opsal et al. |
| 5,963,658 A | 10/1999 | Klibanov et al. |
| 5,970,164 A | 10/1999 | Bamberger et al. |
| 5,999,840 A * | 12/1999 | Grimson et al. ............ 600/424 |
| 6,069,698 A | 5/2000 | Ozawa et al. |
| 6,108,576 A | 8/2000 | Alfano et al. |
| 6,175,407 B1 | 1/2001 | Sartor |
| 6,205,347 B1 | 3/2001 | Morgan et al. |
| 6,208,886 B1 | 3/2001 | Alfano et al. |
| 6,217,847 B1 | 4/2001 | Contag et al. |
| 6,219,566 B1 | 4/2001 | Weersink et al. |
| 6,242,743 B1 | 6/2001 | DeVito et al. |
| 6,252,623 B1 | 6/2001 | Lu et al. |
| 6,264,610 B1 | 7/2001 | Zhu |
| 6,267,477 B1 | 7/2001 | Karpol et al. |
| 6,321,111 B1 | 11/2001 | Perelman et al. |
| 6,332,087 B1 | 12/2001 | Svenson et al. |
| 6,364,829 B1 | 4/2002 | Fulghum |
| 6,373,557 B1 | 4/2002 | Mengel et al. |
| 6,377,353 B1 * | 4/2002 | Ellis ......................... 356/603 |
| 6,381,302 B1 | 4/2002 | Berestov |
| 6,392,241 B1 | 5/2002 | Rushbrooke et al. |
| 6,394,965 B1 | 5/2002 | Klein |
| 6,415,051 B1 | 7/2002 | Callari et al. |
| 6,429,943 B1 | 8/2002 | Opsal et al. |
| 6,529,627 B1 | 3/2003 | Callari et al. |
| 6,549,288 B1 | 4/2003 | Migdal et al. |
| 6,597,931 B1 | 7/2003 | Cheng et al. |
| 6,615,061 B1 | 9/2003 | Khalil et al. |
| 6,615,063 B1 | 9/2003 | Ntziachristos et al. |
| 6,618,152 B2 | 9/2003 | Toida |
| 6,618,463 B1 | 9/2003 | Schotland et al. |
| 6,628,401 B2 | 9/2003 | Toida |
| 6,628,747 B1 | 9/2003 | Schotland et al. |
| 6,636,755 B2 | 10/2003 | Toida |
| 6,642,953 B1 | 11/2003 | Nieto Velasco et al. |
| 6,646,678 B1 * | 11/2003 | Kobayashi ............... 348/207.1 |
| 6,690,520 B1 | 2/2004 | Kusuzawa |
| 6,710,770 B2 | 3/2004 | Tomasi et al. |
| 6,775,567 B2 | 8/2004 | Cable et al. |
| 6,813,030 B2 | 11/2004 | Tanno |
| 6,919,919 B2 | 7/2005 | Nelson et al. |
| 6,963,375 B1 | 11/2005 | Lundberg |
| 7,034,303 B2 | 4/2006 | Schotland et al. |
| 7,184,047 B1 * | 2/2007 | Crampton ................... 345/473 |
| 2003/0011701 A1 | 1/2003 | Nilson et al. |
| 2004/0010192 A1 | 1/2004 | Benaron et al. |
| 2004/0015062 A1 | 1/2004 | Ntziachristos et al. |
| 2004/0021771 A1 | 2/2004 | Stearns |
| 2004/0085536 A1 | 5/2004 | Schotland et al. |
| 2005/0149877 A1 * | 7/2005 | Rice et al. .................. 715/764 |
| 2005/0283071 A1 | 12/2005 | Ripoll et al. |
| 2006/0173354 A1 | 8/2006 | Ntziachristos et al. |

FOREIGN PATENT DOCUMENTS

| | | |
|---|---|---|
| WO | WO97/40381 | 10/1997 |
| WO | WO98/34533 | 8/1998 |
| WO | WO 00/17643 | 3/2000 |
| WO | WO00/36106 | 6/2000 |
| WO | WO00/54581 | 9/2000 |
| WO | WO01/18225 | 3/2001 |
| WO | WO 01/63247 | 8/2001 |
| WO | WO02/41760 | 5/2002 |

OTHER PUBLICATIONS

Weissleder et al., "Shedding Light Onto Live Molecular Targets," Nature Medicine, vol. 9, No. 1, Jan. 2003, pp. 123-128.

Takeda et al., Fourier Transform Method of Fringe-Pattern Analysis for Computer-Based Topography and Interferometry, J. Opt. Soc. Am., vol. 72, No. 1, Jan. 1982.

Toyooka et al., "Automatic Profilometry of 3-D Diffuse Objects by Spatial Phase Detection," Applied Optics, vol. 25, No. 10, May 15, 1986.

Rice et al., "Advances in 2D In Vivo Optical Imaging Instrumentation," Abstract No. 186, Society for Molecular Imaging 2$^{nd}$ Annual Meeting, Aug. 2003.

Frohn, "Super-Resolution Fluorescence Microscopy by Structured Light Illumination," Dissertation submitted to the Swiss Federal Institute of Technology, Zurich, 2000.

Benaron, David A., "A System for Imaging Infection and Gene Expression in the Body in 3-D," Biomedical Optical Spectroscopy and Diagnostics, 1998 Technical Digest, 1998, Optical Society of America, pp. 134-135.

Chang et al., "Improved Reconstruction Algorithm for Luminescence Optical Tomography When Background Lumiphore is Present", Applied Optics, vol. 37, No. 16, Jun. 1, 1998, pp. 3547-3552.

Eppstein et al., "Biomedical Optical Tomography Using Dynamic Parameterization and Bayesian Conditioning on Photon Migration Measurements", Applied Optics, vol. 38, No. 10, Apr. 1, 1999, pp. 2138-2150.

Ghiglia et al., "Two-Dimensional Phase Unwrapping: Theory, Algorithms, and Software", Wiley-Interscience publication, 1998, ISBN 0-471-24935-1, p. 312.

Haskell et al., "Boundary Condition for the Diffusion Equation in Radiative Transfer", Optical Society of America, vol. 11, No. 10, Oct. 1994, pp. 2727-2741.

Ntziachristos et al., "Experimental Three-Dimensional Fluorescence Reconstruction of Diffuse Media by Use of a Normalized Born Approximation", Optical Society of America, vol. 26, No. 12, Jun. 15, 2001, pp. 893-895.

Research & Development (magazine), vol. 42, No. 9, Sep. 2000, Part 1 of 2.

Rice et al., "In Vivo Imaging of Light-Emitting Probes", Journal of Biomedical Optics, vol. 6, No. 4, Oct. 2001, p. 432-440.

Yang et al., "Whole-Body Optical Imaging of Green Fluorescent Protein-Expressing Tumors and Metastases", PNAS, vol. 97, No. 3, Feb. 1, 2000, pp. 1206-1211.

* cited by examiner

//www.w3.org/1999/xhtml">
STRUCTURED LIGHT IMAGING APPARATUS

CROSS-REFERENCE TO RELATED APPLICATION

This application claims priority under 35 U.S.C. §120 from U.S. patent application Ser. No. 09/905,668, filed Jul. 13, 2001 now U.S. Pat. No. 7,113,217 and titled "Multi-View Imaging Apparatus", which is incorporated herein by reference for all purposes.

FIELD OF THE INVENTION

The present invention relates generally to imaging systems and their methods of use. More specifically, the present invention relates to imaging systems that include a structured light source.

BACKGROUND OF THE INVENTION

One new type of imaging involves the capture of low intensity light from an object. A source of the light indicates a portion of the object where an activity of interest may be taking place. In one example, the object is a small animal such as a mouse and the light source includes tumor cells labeled with light emitting reporters such as firefly luciferase or fluorescent proteins or dyes. This technology is known as in vivo optical imaging.

Tomographic reconstruction in in vivo imaging builds a three-dimensional representation of the internal light source inside the surface of the object. Some tomographic reconstruction techniques rely on a three-dimensional representation of the object surface. Imaging small animals such as a mouse may require a new surface representation for each animal and each time the animal is imaged.

A system that allows a user to readily obtain a surface representation of an object is not currently available.

SUMMARY OF THE INVENTION

The present invention integrates a structured light source into an imaging system for reconstructing a surface topography of an object being imaged. The structured light source includes a mechanism for transmitting a set of lines onto the object from an angle. The lines are displaced, or phase shifted relative to a stage, when they encounter an object with finite height, such as a mouse. This phase shift provides structured light information for the object. A camera captures the structured light information. Using software that employs a structured light analysis, surface topography data for the object (over its entire surface or a portion) is determined from the phase shift of the lines.

In one aspect, the present invention relates to an imaging system for providing a three-dimensional surface representation of an animal. The imaging system comprises an imaging chamber including a set of walls enclosing an interior cavity and including a camera mount configured to position a camera. The imaging system also comprises a stage configured to support the animal within the interior cavity and within a field of view for the camera. The imaging system further comprises a structured light source configured to produce structured light for transmission onto the animal while the animal rests on the stage. This generates structured light surface information for the animal. The imaging system additionally comprises a processor configured to produce a three-dimensional surface representation of at least a portion of the animal using the structured light surface information obtained by the camera.

In another aspect, the present invention relates to an imaging system for providing a three-dimensional representation of an animal. The imaging system comprises a moveable stage apparatus including a transport mechanism and a stage configured to support the animal within the interior cavity. The stage is coupled with the transport mechanism for movement of the animal to one of a plurality of positions in the interior cavity. The imaging system also comprises a structured light source configured to produce structured light for transmission onto the animal while the animal rests on the stage to generate structured light surface information for the animal.

In yet another aspect, the present invention relates to an imaging system for providing a three-dimensional representation of an animal. The imaging system comprises a structured light source configured to produce a grid of light lines for transmission onto the animal.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 6B-6H illustrate pictorial representations of structured light imaging corresponding to the process flow of FIG. 6A.

DETAILED DESCRIPTION

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, procedures, components, and circuits have not been described in detail so as not to unnecessarily obscure aspects of the present invention.

Overview

The present invention relates to imaging systems that comprise a structured light source, which produces structured light for transmission onto an object, such as a small animal. Structured light uses a set of lines of light. In one embodiment, the set of lines is projected down on an object at an angle (at about 30 degrees, for example) to the surface normal. The object generates structured light surface information as each light line reacts to the shape of the animal. Cumulatively, the lines of light each bend or alter in spacing as they pass over the object (FIG. 6C). The structured light surface information can be measured and used to determine the height of the surface at all locations that are illuminated by the structured light source.

A camera captures the structured light surface information, digitizes the information and produces one or more structure light images. A processor produces a three-dimensional surface representation of the object—or a portion of the object facing the camera—using the structured light information. More specifically, a processing system, running on stored instructions for generating a topographic representation (a surface map) from the structured light surface information, builds a 3D topographic representation of the object using the structured light surface information. Various reconstruction techniques may be stored in software and used to build a 3D topographic representation. In one embodiment, the surface topography reconstruction produces a surface mesh.

Structured Light Source

Figure 1:
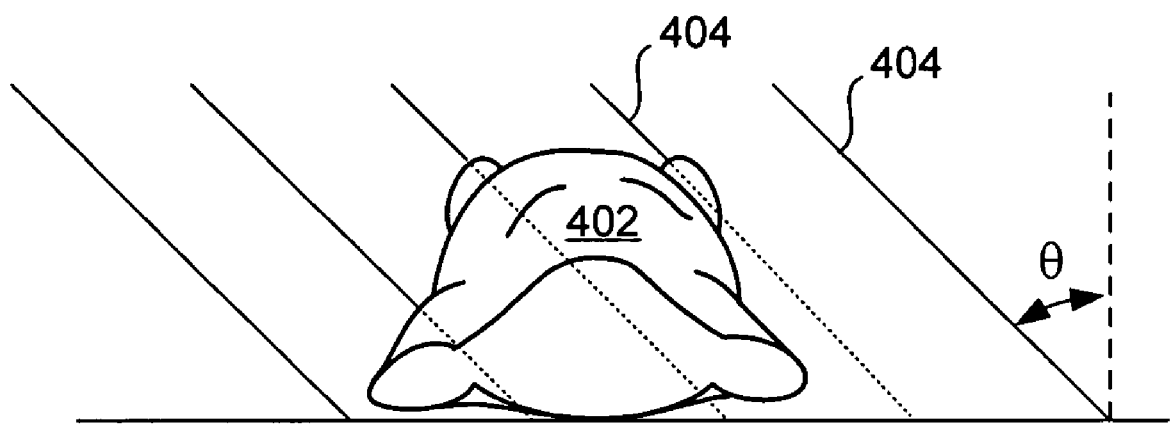
FIG. 1 illustrates a simplified view of structured light transmission from an angle.

FIG. 1 illustrates the projection of structured light onto an object and the generation of structured light surface information. A light source of the present invention transmits light onto an object 402 in one or more lines 404 at an angle, θ. Since the projection angle is known, horizontal displacement for each line 404 is related to the height of object 402. More specifically, the height of object 402 where it intercepts each line 404 generates structured light information for each line 404 according to the horizontal displacement caused on the incoming light. By transmitting a grid of lines 404 of known dimensions onto the facing surface of object 402, a map of the facing surface topography may be obtained by quantitatively assessing horizontal bends in the captured light. FIG. 6C illustrates bends in a grid of lines cast onto a mouse sample. The structured light surface information then includes differences between the known spacing for the transmitted array of lines without any interference and the observed pattern captured by the camera. Although the present invention will be described with respect to horizontal differences in the structured light for a horizontal surface normal, it is understood that other systems may transmit structured light from other angles that produce structured light information in another direction (e.g., a vertical surface normal or any angle between a horizontal surface normal and vertical surface normal).

The angle of incidence relative to the surface normal may vary. In one embodiment, an angle from about 15° to about 30° is suitable. Angles greater or less than this range may also be used. Preferably, the projection angle is large enough to get sufficient "bend" in the lines to achieve spatial resolution, but small enough that large shadows are not present.

Light output by a structured light source of the present invention may vary. In general, the light output may include any lines or shapes suitable for generating structured light surface information that is useful in building a surface topography. In one embodiment, a structured light source transmits a grid of lines onto the animal. Line spacing between line in a parallel grid may be adapted to a specific object or image. A structured light source producing a parallel grid of lines having a line spacing in the range of about 0.5 to about 2 lines per mm is suitable for a mouse. Other line spacings are suitable for use with the present invention. Closer line spacing provides higher resolution, but the lines may be more difficult to track on rough surfaces such as fur. The line spacing may also vary based on the object surface texture and object size.

The present invention may use any suitable structured light generating system. In one embodiment, a structured light source used in an imaging system includes a projector that projects a grid of lines 404. In another embodiment, a structured light source includes a laser operatively cooperating with a pair of actuated mirrors that rapidly move a single light beam to form the set of lines across the object 402. Another suitable structured light projector comprises a laser device that employs diffraction patterns to achieve a desired structured light pattern. Other structured light sources may be used with the present invention.

Figure 2A:
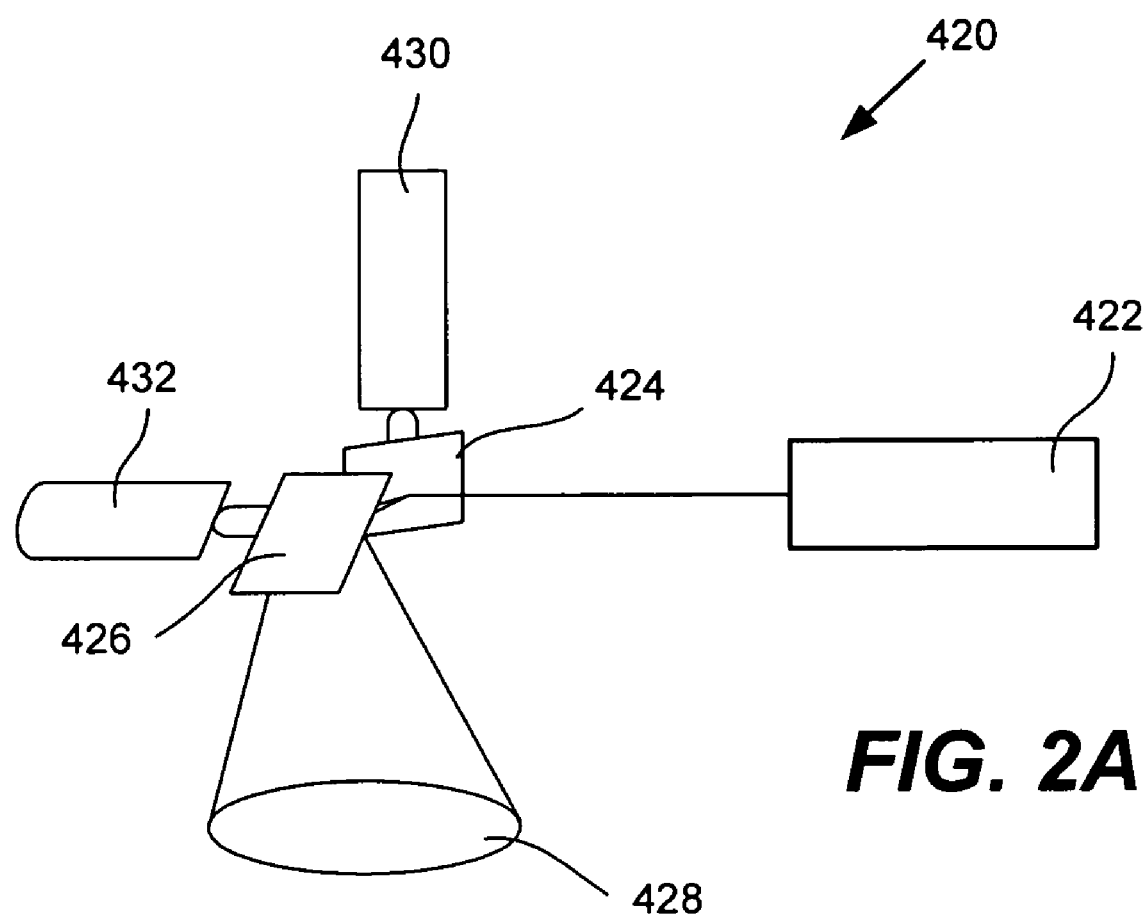
FIG. 2A illustrates a structured light source comprising a scanning laser galvanometer in accordance with one embodiment of the present invention.

FIG. 2A illustrates a structured light source comprising a scanning laser galvanometer 420 in accordance with one embodiment of the present invention. Scanning laser galvanometer 420 comprises a laser 422 and a pair of mirrors 424 and 426.

Laser 422 generates light. Laser 422 is positioned such that output of its linear laser beam transmits onto mirror 424.

Laser 422 may include any suitable laser, such as a diode laser or a diode pumped solid-state laser. Any color is also suitable for use with laser 422. Common commercially available laser colors include red, green and blue. In a specific embodiment, laser 422 comprises a green diode pumped solid-state laser, such as one available from a wide variety of commercial vendors.

Mirrors 424 and 426 each direct light provided by laser 422. As shown, mirror 424 first receives light provided by laser 422 and reflects the light towards mirror 426, which reflects the light into an imaging chamber. The two mirrors cooperate to permit two degrees of freedom for positioning a light beam provided by laser 422. A maximum transmission field 428 defines the spatial range for direction of light by mirrors 424 and 426. Mirrors 424 and 426 may create any line, shape, grid or pattern of light within field 428. For example, the actuators and mirrors 424 may form a set of parallel lines normal to the head to toe facing of a mouse (for any position of the mouse). In one embodiment, mirrors 424 and 426 receive position control from a computer that determines a specific light pattern output by scanning laser galvanometer 420.

Actuators 430 and 432 position mirrors 424 and 426, respectively. Each actuator 430 and 432 may comprise any suitable mechanical actuation responsive to electrical input. For example, motors are suitable for use with actuators 430 and 432. In another specific example, magnetic actuation is suitable for use with actuators 430 and 432. Magnetic actuation provides accurate and rapid response. For galvanometer 420, the actuators operate at a high enough speed such that a single beam of light produced by laser 422 may generate a set of lines. In this case, the mirrors move fast enough such that the laser point sweeps across the surface of the animal quickly enough to register lines as detected by a camera. In a specific embodiment, the grid of lines comprises about one hundred lines and the entire grid is scanned every $\frac{2}{10}$ths of a second. Grids of more or less lines are also suitable, as are other scan rates.

In one embodiment, scanning laser galvanometer 420 is custom-designed for use in an imaging chamber of the present invention. In another embodiment, scanning laser galvanometer 420 comprises a commercially available model. One exemplary scanning laser galvanometer system suitable for use with the present invention is a model 6200H galvanometer scanner and a 67120-0627 MicroMax Model 671XX Servo Driver and Controller as provided by Cambridge Instruments of Cambridge, Mass.

Computer control of mirrors 424 and 426 for scanning laser galvanometer 420 also permits custom light output for a structured light source. For example, this permits line spacing to be altered and finely controlled. In this case, computer control may allow a user to increase the density of line spacing and increase the amount of structured light surface information, which results in a more detailed topographic representation. Computer control also permits control of structured light patterns to improve the quality of structured light surface information for an animal. For example, computer-control permits the line spacing to vary to accommodate variations in animal size and fur color or texture for an animal. Computer control also permits control of structured light patterns to adapt for a particular field of view used in imaging or orientation of the animal.

Independent control of each mirror 424 and 426 also permits a user to steer the light to different locations within the imaging chamber. This is useful when a user places an animal or object in an off-center position. In addition, this is useful when multiple animals are imaged within an imaging box.

The projected light pattern produced by scanning laser galvanometer 420 may also be used for other purposes. For example, the projected pattern may be used to generate an alignment target for positioning an object or animal within the imaging chamber. In this case, scanning laser galvanometer 420 creates crosshairs or another suitable alignment target for positioning an animal on a stage or floor of the imaging chamber. The light output may also indicate the field of view for the camera.

In addition, scanning laser galvanometer 420 may be used for automated focusing techniques. More specifically, displacement of grid lines on the top surface of a mouse may indicate how tall the mouse is. Since each mouse may be a different height, this provides an automated focus system for the imaging system that permits the camera to adaptively focus to a specific height for each individual mouse.

Since mirrors 424 and 426 permit flexible re-direction and transmission of light, scanning laser galvanometer 420 may be flexibly located in an imaging chamber. In one embodiment, scanning laser galvanometer 420 is disposed at the top of an imaging chamber and reflects the laser beam of light down onto a top surface of the animal. When galvanometer 420 is disposed outside a top wall 423 (or sub-wall) of the imaging chamber (see FIG. 2B), the top wall includes a small hole 421 that permits light from the second mirror to pass through and into the imaging chamber. Proximity between the second mirror and wall 423 reduces size of hole 421, since any structured light pattern or other pattern splaying at some projection angle has not had significant distance to enlarge.

Scanning laser galvanometer 420 may be implemented flexibly in a number of light imaging systems. In one embodiment, scanning laser galvanometer 420 is disposed above an animal to be imaged and casts light down onto the animal at an angle.

Figure 2B:
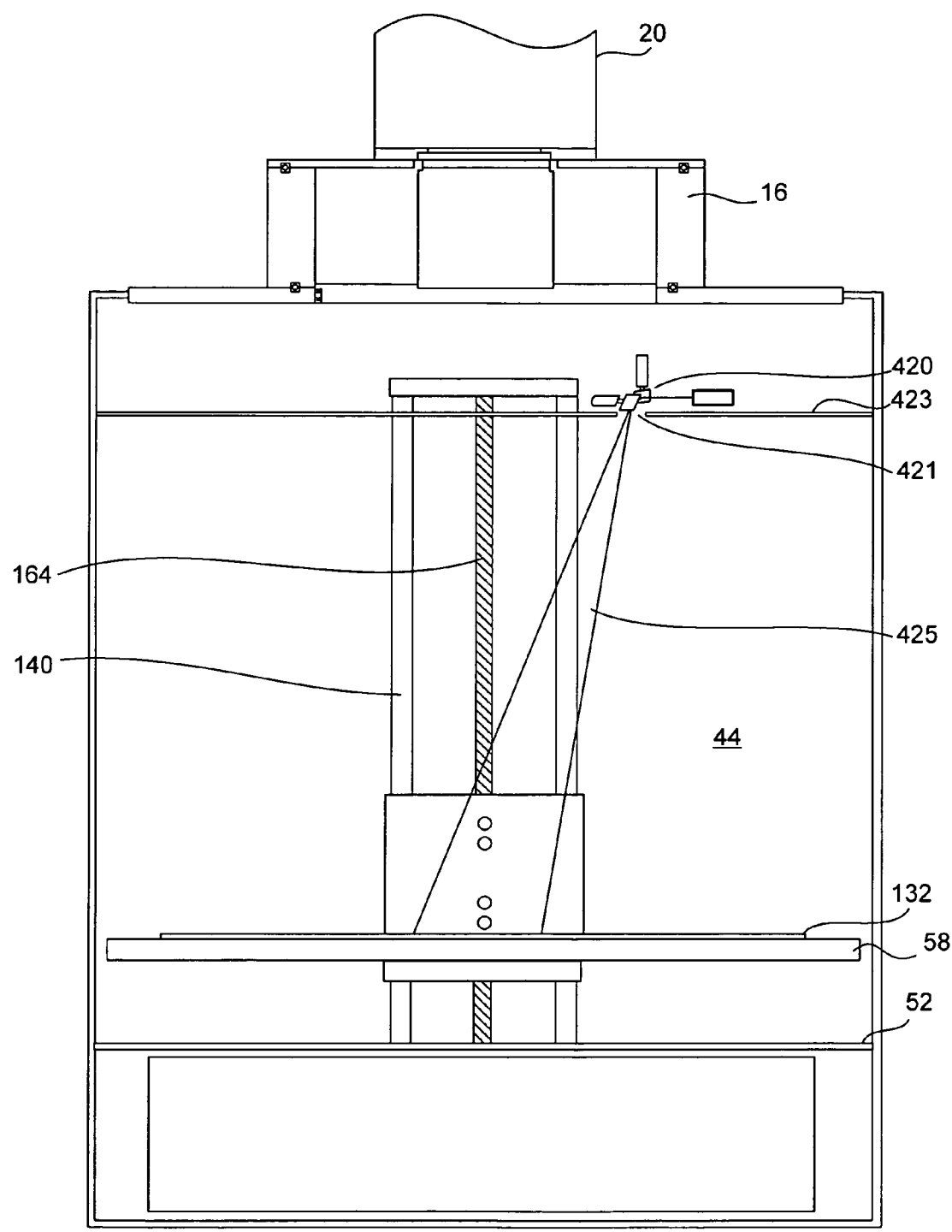
FIG. 2B illustrates a stage internal to an imaging box that includes the scanning laser galvanometer of FIG. 2A in accordance with one embodiment of the present invention.

FIG. 2B illustrates a simplified cross section of a stage internal to an imaging box that includes the scanning laser galvanometer 420 in accordance with one embodiment of the present invention. The imaging box is illustrated with a movable stage 58. In another embodiment, stage 58 is stationary and comprises the bottom surface of an imaging chamber.

Movable stage 58 supports an object to be imaged. Movable stage 58 is capable of linear, reciprocal movement between a bottom partition 52 and a top enclosure panel, and may be retained at any position therebetween for image capture. Thus, moveable stage 58 has a multiple vertical positions in imaging chamber 44 having the substantially same horizontal position. In a specific embodiment, movable stage 58 has a threaded bore that is operably engaged with a worm gear 164 that provides vertical translation of the moveable stage 58. A motor drives the worm gear to move the stage 58 up and down along a pair of guides 140. In another embodiment, the stage 58 is driven vertically using a belt driven system that provides a faster response than the worm gear. A temperature control element 132 is provided by a heating blanket placed on top of stage 58 for controlling the temperature of a mammal placed on stage 58. In one embodiment, temperature-adjusting element 132 includes a thermal sheet that is fixed, e.g. glued, into a cut-away portion of stage 58.

Scanning laser galvanometer 420 projects structured light 425 onto the top surface of stage 58 (or the temperature control element 132 thereon). The size of a grid produced on stage 58 (or an animal resting thereon) will depend on the position of stage 58 and control of each mirror 424 and 426 according to a desired grid size.

Figure 3A:
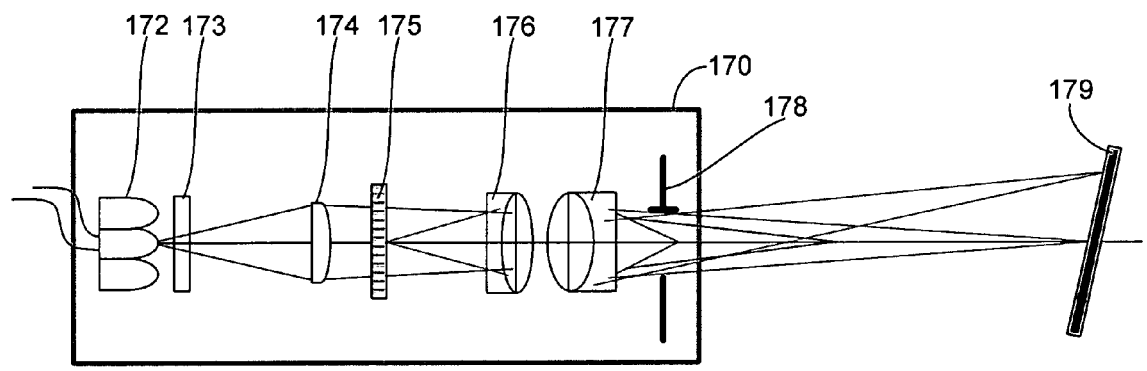
FIG. 3A shows internal components of a structured light projector used to produce structured light in accordance with one embodiment of the present invention.

In another embodiment, a structured light source includes a light projector. FIG. 3A illustrates internal components of a structured light projector 170 in accordance with another embodiment of the present invention. Structured light projector 170 comprises a light source and a filter or mask that creates a structured light pattern. In this case, structured light projector 170 includes a Kohler illumination system where a slide is illuminated by a light source and then an image of the slide is projected onto the sample or background. As shown, structured light projector 170 includes LEDs 172, diffuser 173, condenser 174, mask 175, lenses 176 and 177, and aperture 178.

LEDs (light emitting diodes) 172 generate light. In a specific embodiment, LEDs 172 include multiple LEDs of a single color, such as green. Any color light suitable is suitable for use. LEDs 172 may include any appropriate number of light emitting diodes to generate sufficient light for creation of a grid pattern. Diffuser 173 reduces spatial variance in the intensity of light across its surface area to produce light flux at its output surface that has a more even light intensity distribution across the flux area. LEDs 172 and diffuser 173 cumulatively provide light of a desired flux with substantially equal intensity distribution.

Condenser receives light from diffuser 173, condenses the divergent light flux from LEDs 172 and transmits the light onto mask 175. Mask 175 includes a number of apertures that selectively permit the passage of light therethrough. As shown, mask 175 includes a series of parallel lines that form a parallel line grid. The spacing and number of lines may vary as described above. Other patterns may be formed by mask 175 other than parallel lines. The light output of mask 175 resembles a structured light grid cast onto an object or surface for structured light imaging.

Lenses 176 and 177 combine to project and cast the light output of mask 175 onto a desired surface. Output from lenses 176 and 177 travels through aperture 178 and forms the output of structured light projector 170. In one embodiment, the grid of lines output from projector 170 is cast directly onto the imaging surface. In another embodiment, the grid of lines output from projector 170 is cast onto one or more projector mirrors 179 before transmission onto an object and the imaging surface. In one embodiment, the grid lines are then projected onto the animal stage with a magnification of approximately 10×. Aperture 178 controls the size of the pattern leaving projector 170. In one embodiment, aperture 178 is variable and computer controlled.

Although FIG. 3A illustrates one specific embodiment of a structured light projection source, other structured light projection sources are also suitable for use with the present invention.

Figure 3B:
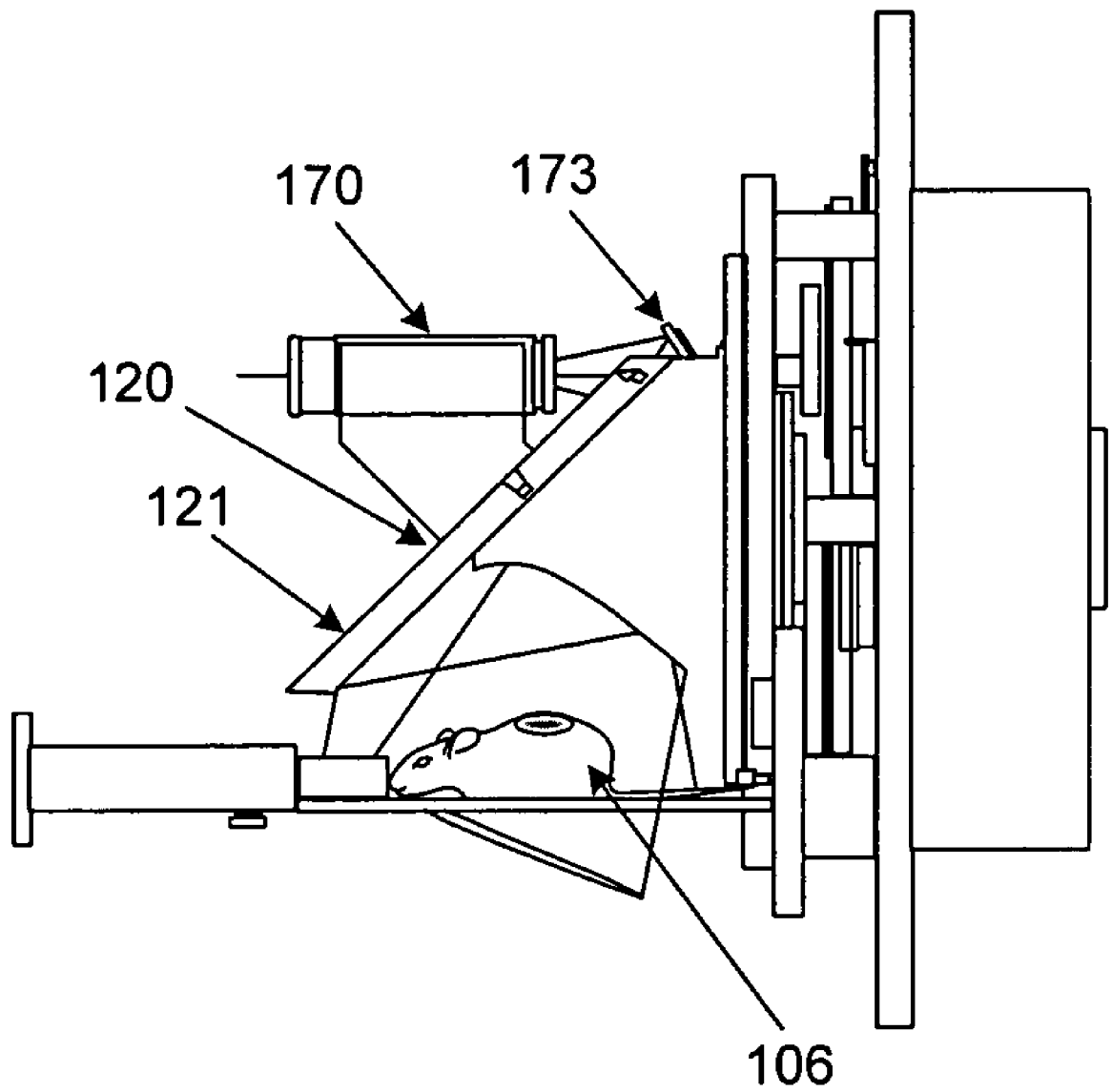
FIG. 3B shows the configuration of the structured light projector used to obtain the subject surface topography.

FIG. 3B shows structured light projector 170 attached to and rotating with a light transport device 120 in accordance with one embodiment of the present invention. Structured light projector 170 produces a grid of light lines for transmission onto animal 106 while the animal rests on a stage to generate structured light surface information for the animal. In a specific embodiment, structured light projector 170 consists of a Kohler illumination system where a slide is illuminated by a light source and then an image of the slide is projected onto the animal.

Figure 3C:
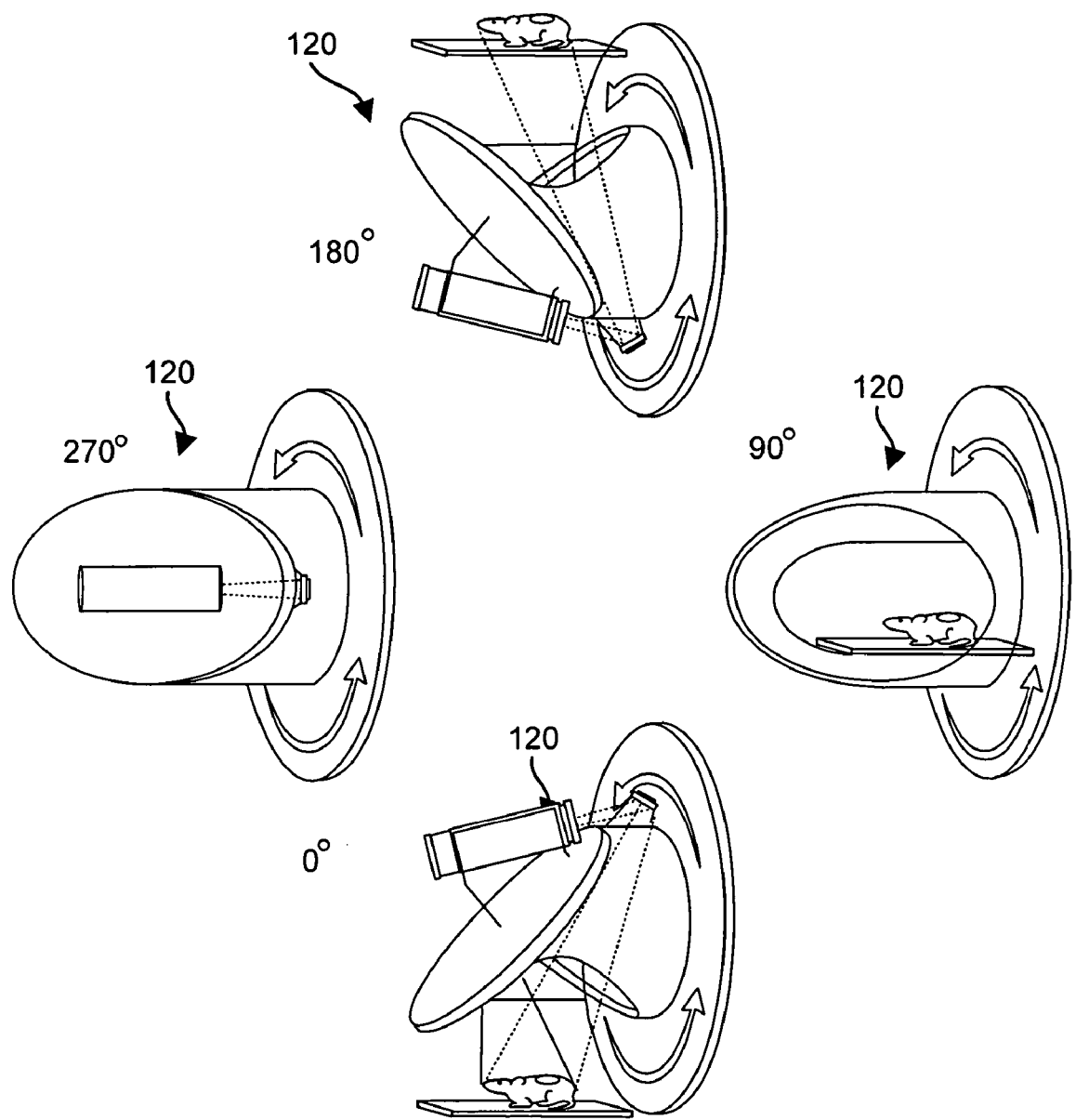
FIG. 3C shows four different example positions of the stage relative to the light transport device of FIGS. 3D and 3E: 0 degrees, 90 degrees, 180 degrees, and 270 degrees.
Figure 3D:
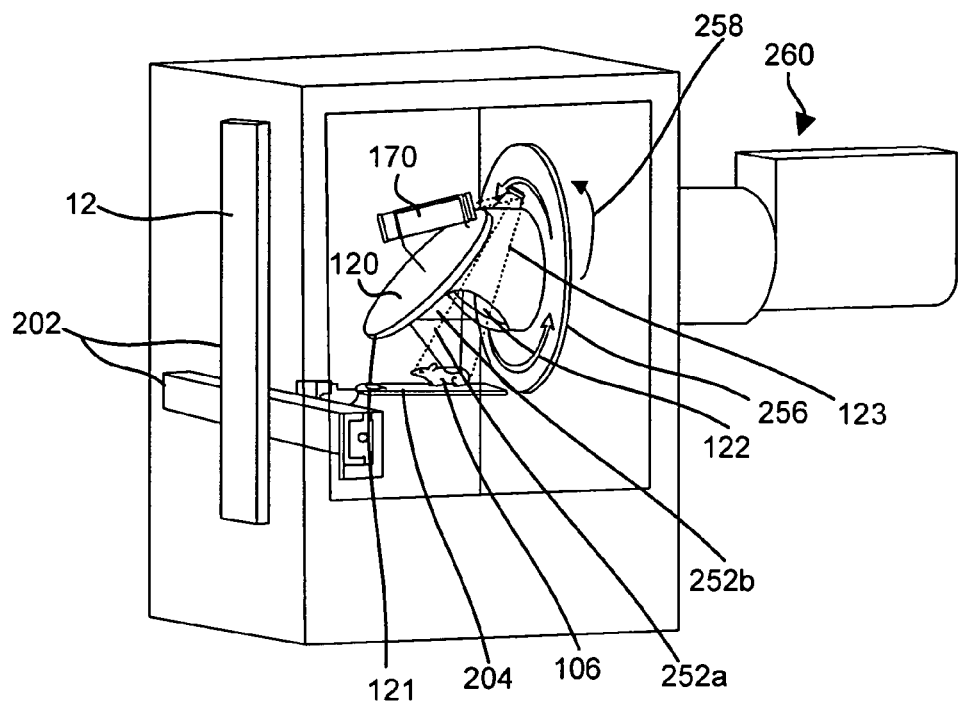
FIG. 3D is a cut away perspective view of an imaging having internal components for facilitating multiple views of the sample in accordance with one embodiment of the present invention.
Figure 3E:
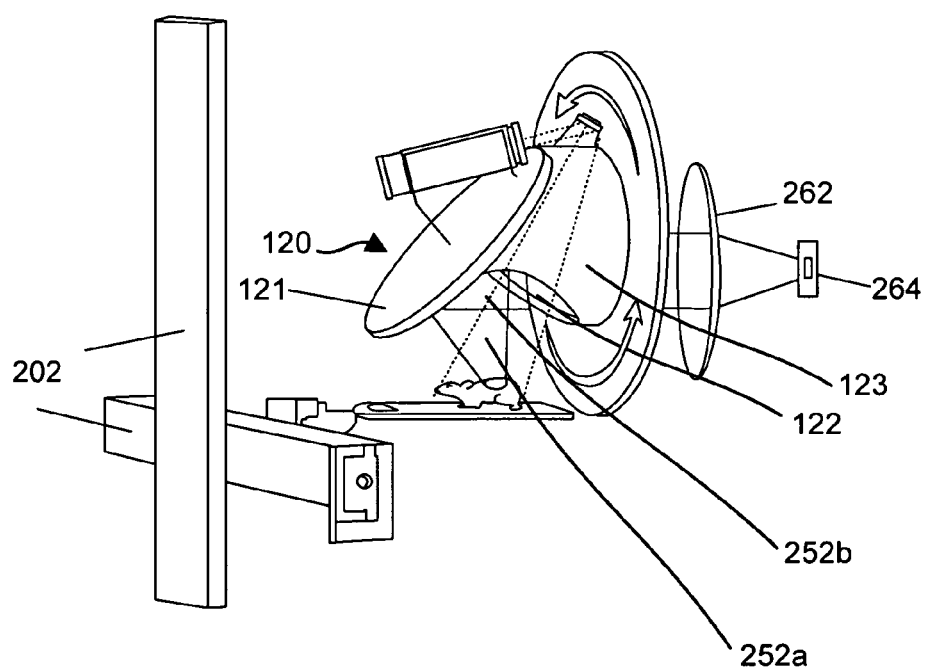
FIG. 3E is a perspective view of the internal components of FIG. 3D for facilitating multiple views of the sample in accordance with one embodiment of the present invention.

The projector module 170 rides on the back of the rotating light transport device 120 (see FIGS. 3C-3E for operable rotation of device 120), so that lines are always projected on the sample 106 at all viewing angles. The illumination pattern is projected horizontally and reflects off of a projector mirror 173 at the base of the larger turning mirror to illuminate sample 106. FIGS. 7A-7D describe another embodiment of projector module 170 attached to the back of the rotating light transport device 120 in more detail.

Exemplary Imaging Systems

In one aspect, the present invention relates generally to improved imaging systems that employ a structured light source. Several embodiments of imaging systems in which are suitable for implementing the techniques of the present invention are described further in U.S. patent application Ser. No. 09/905,668 filed by Nilson et al. on Jul. 13, 2001, entitled MULTI-VIEW IMAGING APPARATUS. The entire disclosure of this application is incorporated herein by reference for all purposes.

Figure 4A:
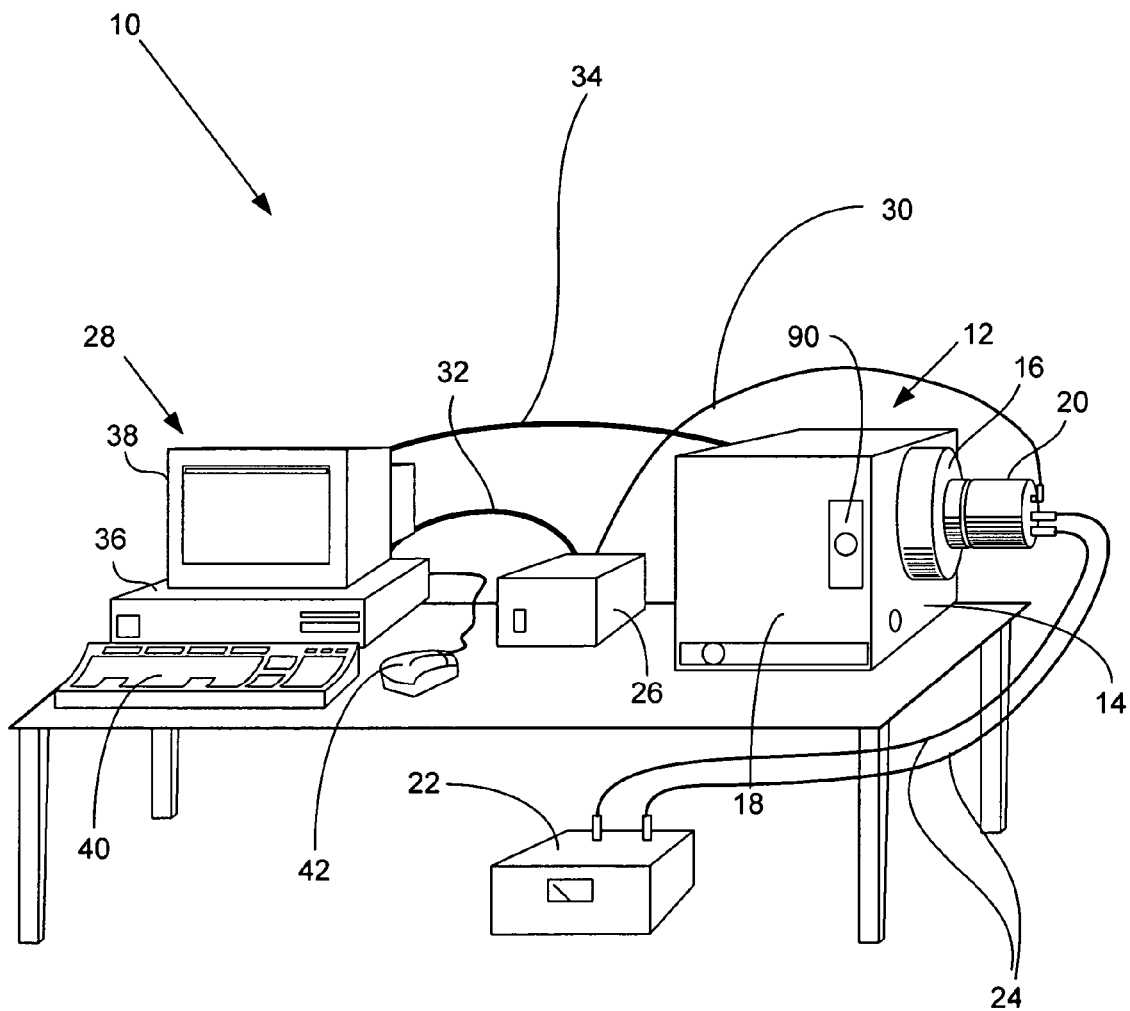
FIG. 4A is a perspective view of an imaging system including an imaging box adapted to capture images in accordance with one embodiment of the invention.

FIG. 4A illustrates an imaging system 10 adapted to capture photographic, structured light and luminescence images in accordance with one embodiment of the present invention. While specific examples and components of an imaging system will now be described, the present invention is not limited to the specific imaging systems described herein and may comprise more and less complex systems.

System 10 provides user automated control of image capture in an imaging box 12. Imaging system 10 is also useful for capturing and constructing structured light images. Imaging system 10 comprises an imaging box 12 adapted to receive a light-emitting object in which low intensity light, e.g., luciferase-based luminescence, is to be detected. Imaging box 12 includes a housing 16 on a side vertical wall of the box having a camera mount 109 adapted to receive a camera. Imaging box 12 is configured to be "light-tight", i.e., essentially all external light is prevented from entering the box 12 from the ambient room.

A high sensitivity camera, e.g., an intensified or a charge-coupled device (CCD) camera 20, is attached to the imaging box 12 preferably through the camera mount affixed to housing 16. CCD camera 20 captures photographic, structured light and luminescent images of the object within the imaging box 12. CCD camera 20 may optionally be cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other refrigerants, such as liquid nitrogen or solid state devices, may be used to cool the CCD camera 20.

An image processing unit 26 optionally interfaces between camera 20 and a processing system 28 through cables 30 and 32, respectively. Processing system 28, which may be of any suitable type, typically comprises a main unit 36 that contains hardware including a processor, memory components such as random-access memory (RAM) and read-only memory (ROM), and disk drive components (e.g., hard drive, CD, floppy drive, etc.). System 10 also includes a display 38 and input devices such as a keyboard 40 and mouse 42. Processing system 28 is in communication with various components in the imaging box 12 via one or more cables 34. System 28 may also include additional imaging hardware and software, structured light software, and image processing logic and instructions for processing information obtained by camera 20. For example, stored instructions run by processing system 28 may include instructions for i) receiving structured light information, and ii) building a 3D tomographic representation of the object in box 12 using structured light surface information obtained by camera 20 while the animal rests on a stage, as will be described in further detail below.

To provide control of various components, processing system 28 includes suitable processing hardware and software configured to provide output for controlling any of the devices in the imaging box 12. The processing hardware and software may include an I/O card, control logic for controlling any of the components of the imaging system 10, and a suitable graphical user interface for the imaging system 10. Processing system 28 also includes suitable processing hardware and software for camera 20 such as additional imaging hardware, software, and image processing logic for processing information obtained by camera 20. Components controlled by processing system 28 may include camera 20, the motors responsible for camera 20 focus, one or more motors responsible for position control of a stage supporting the sample, the camera lens, f-stop, etc. The logic in processing system 28 may take the form of software, hardware or a combination thereof. System 28 also communicates with a display 38 for presenting imaging information to the user. By way of example, the display 38 may be a monitor, which presents a measurement graphical user interface (GUI). The graphical user interface allows a user to view imaging results and also acts an interface to control the imaging system 10. One suitable imaging software includes "LivingImage" as provided by Xenogen Corporation of Alameda, Calif.

System 10 provides both topographic and tomographic imaging tools. Topographic imaging refers to the surface characterization of an object. The present invention uses structured light to determine surface topography for an object. Tomographic imaging refers to information inside the surface. This is useful for localizing internal objects in three dimensions inside an object, for example. An exemplary illustration of these two imaging forms uses a 2D planar slice through an object: topography gives the surface (the outer bounding line), while tomography gives everything inside the bounding surface.

Processing system 28 is configured to produce a three-dimensional surface representation of an animal using structured light surface information obtained by camera 20. Typically, a processor produces the three-dimensional surface representation using instructions stored in memory that determine how to produce the three-dimensional surface representation from the structured light surface information. Further description of one suitable method and its specific steps taken by a processor to convert structured light information into a three-dimensional surface representation are described below with respect to FIG. 6B. Other systems convert structured light surface information into a three-dimensional surface representation are known to those of skill in the art. Thus, systems of the present invention are not limited to how a processor produces a three-dimensional surface representation of an animal using the structured light surface information obtained by the camera.

Imaging system 10 is suitable for capturing images from a variety of views and positions of the object relative to camera 20. These images may be used in in-vivo imaging applications that include analysis of one or more representations of emissions from internal portions of a specimen superimposed on a photographic representation of the specimen. In one embodiment, imaging system 10 is used for 2-D, 3D and structured light imaging of a low intensity light source, such as luminescence from luciferase-expressing cells, fluorescence from fluorescing molecules, and the like. The low intensity light source may be emitted from any of a variety of light-emitting objects or samples which may include, for example, tissue culture plates, multi-well plates (including 96, 384 and 864 well plates), and animals containing light-emitting molecules. Animals may include any mammal, such as a mouse, cat or rat for example.

In one embodiment, the object is a mouse containing light producing cells. The resulting luminescence image may therefore be captured without using any light sources other than the object itself. Luminescence from the object is recorded as a function of position to produce the luminescence image. One approach to generating such composite photographic/luminescence images is described in U.S. Pat. No. 5,650,135 issued to Contag et al. on Jul. 22, 1997. The entire disclosure of that patent is incorporated herein by reference for all purposes.

In one particular embodiment, a 2-D or 3D luminescence image represents a collection of emitted photons received by each detector pixel of the CCD camera 20 over a defined length of time. In other words, the luminescence image may display magnitude values representing the photon counts at the individual detector pixels. Regions of the object emitting radiation (e.g., photons) will appear in the luminescence image. The luminescence images may indicate the presence of a biocompatible entity, for example. The entity can be a molecule, macromolecule, cell, microorganism, a particle or the like. Thus, an in-vivo analysis may include detecting localization of a biocompatible entity in a mammalian subject.

Figure 4B:
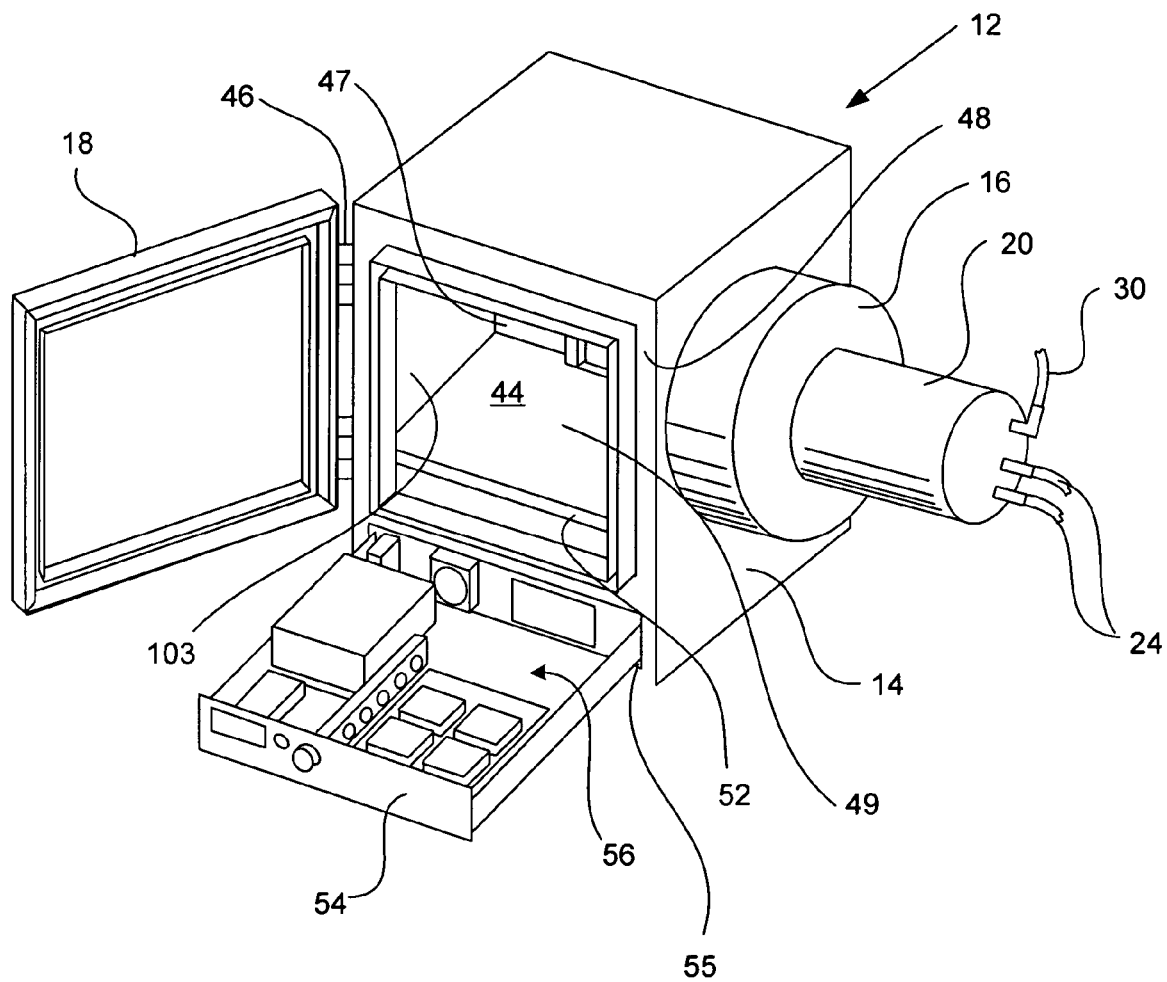
FIG. 4B illustrates the structural components of the imaging box of FIG. 4A.

FIG. 4B illustrates components of imaging box 12 of FIG. 4A in accordance with one embodiment of the present invention. As shown in FIG. 4B, imaging box 12 is illustrated with a door 18 in an open position, showing an imaging chamber 44 for receiving the object. Imaging chamber 44 is defined by opposing side enclosure panels 103, a light-tight partition 52 on the bottom, a top panel (not shown), a back enclosure panel 47, and a front wall 48 defining a cavity opening 49 into the imaging chamber 44.

Below chamber 44 is a smaller compartment separated therefrom by the light-tight partition 52, the upper surface of which serves as a floor for imaging chamber 44. In one embodiment, the smaller compartment provides a housing space which is adapted to slideably receive a drawer 54 though a front opening 55 formed in the body 14. The drawer 54 houses electronic components 56 which are in electrical communication with processing system 28 (FIG. 4A) and control various components and functions of the box 12. In a specific embodiment, the imaging box 12 has a body 14 made of a suitable metal such as steel.

A latchable door 18 is pivotally attached to box body 14 by way of hinges 46 which permit the door 18 to be moved from the closed position as shown in FIG. 4A to the open position as shown in FIG. 4B. In the open position, door 18 enables user access to the cavity 44 through the opening 49. In the closed position, door 18 prevents access to the cavity interior 44 through the cavity opening 49.

Figure 4C:
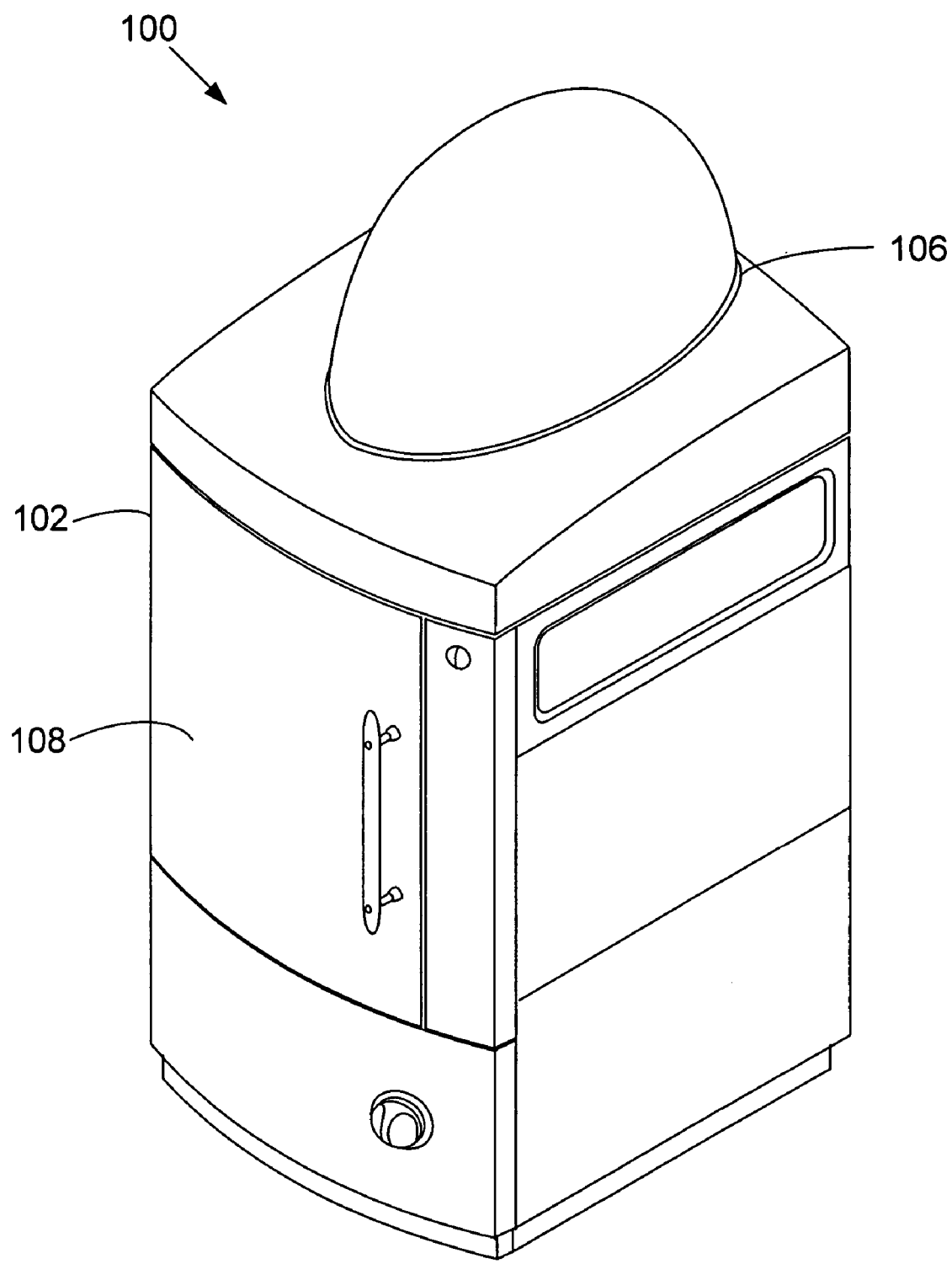
FIGS. 4C and 4D illustrate a perspective view of an imaging system in accordance with another embodiment of the present invention.

FIG. 4C illustrates an imaging system 100 in accordance with another embodiment of the present invention. Imaging system 100 comprises a combined design that includes components of system 10 in a single structure.

Imaging system 100 comprises an imaging box 102 having a door 108 and inner walls 109 (FIG. 4D) that define an interior cavity 201 that is adapted to receive a light-emitting object. Imaging box 102 is suitable for imaging including the capture of low intensity light on the order of individual photons, for example. Imaging box 102 seals out essentially all of the external light from the ambient room from entering the box 102, and may include one or more seals that prevent light passage into the box when door 108 is closed. In a specific embodiment, door 108 comprises one or more light-tight features such as a double baffle seal, while the remainder of chamber 102 is configured to minimize any penetration of light into cavity 201. Objects for structured light imaging are placed within box 102 by opening door 108, inserting the object in chamber 201, and closing door 108. One suitable imaging system is the IVIS® Imaging System 200 Series as provided by Xenogen Corporation of Alameda, Calif.

Figure 4D:
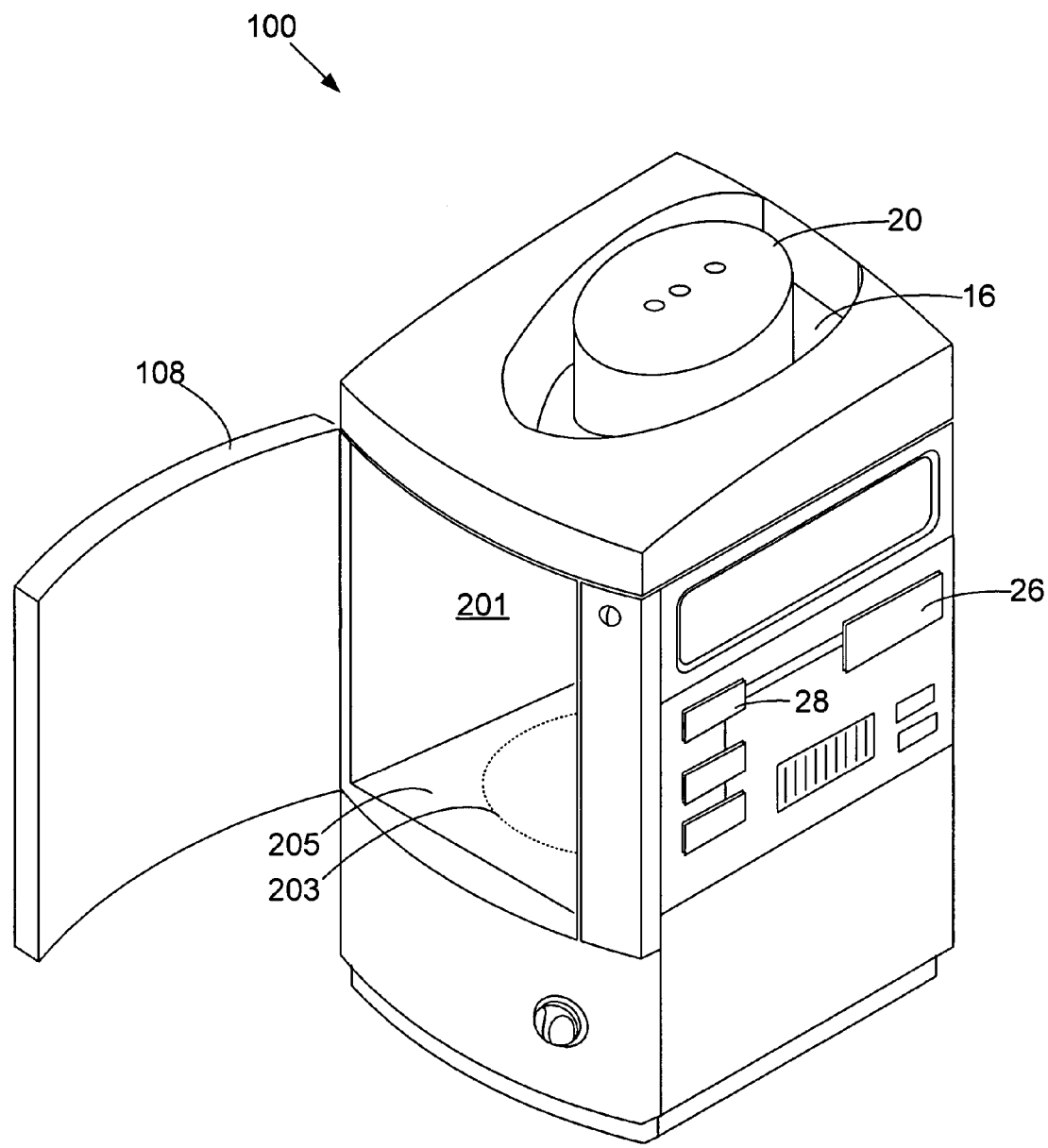

Imaging box 102 includes an upper mounted camera 20. Housing 106 is adapted to receive camera 20 (FIG. 4D). Imaging system 100 may also comprise a lens (not shown) that collects light from the specimen or phantom device and provides the light to the camera 20. A stage 205 forms the bottom floor of imaging chamber 201 and includes motors and controls that allow stage 205 to move up and down to vary the field of view 203 for camera 20. A multiple position filter wheel may also be provided to enable spectral imaging capability. Imaging box 102 may also include one or more light emitting diodes on the top portion of chamber 201 to illuminate a sample during photographic image capture. Other features may include a gas anesthesia system and heated sample shelf to maintain an animal's body temperature during image capture and anesthesia.

FIG. 4D shows system 100 with the removal of a side panel for imaging box 102 to illustrate various electronics and processing components included in system 100. Imaging system 100 comprises image processing unit 26 and processing system 28.

Imaging System Operation and Structured Light Capture

The present invention may be employed in a wide variety of imaging applications. Generally, the present invention may be applied with any non-invasive methods and compositions for detecting, localizing and tracking light-emitting entities and biological events in a mammalian subject. For example, the imaging system 10 may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of box 12 and on stage 204. Camera 20 is then activated to detect the emitted photons. The photon signal may then be used to construct a luminescent image of photon emission. The luminescent image is constructed without using light sources other than the luminescence from the object itself. This luminescence is recorded as a function of position to produce the luminescence image. The photographic image may also be taken of the same object to aid in position visualization of the luminescent image. One approach to generating such composite photographic/luminescence images is described in U.S. Pat. No. 5,650,135 issued to Contag et al. on Jul. 22, 1997. The entire disclosure of that patent was previously incorporated herein by reference.

Figure 5:
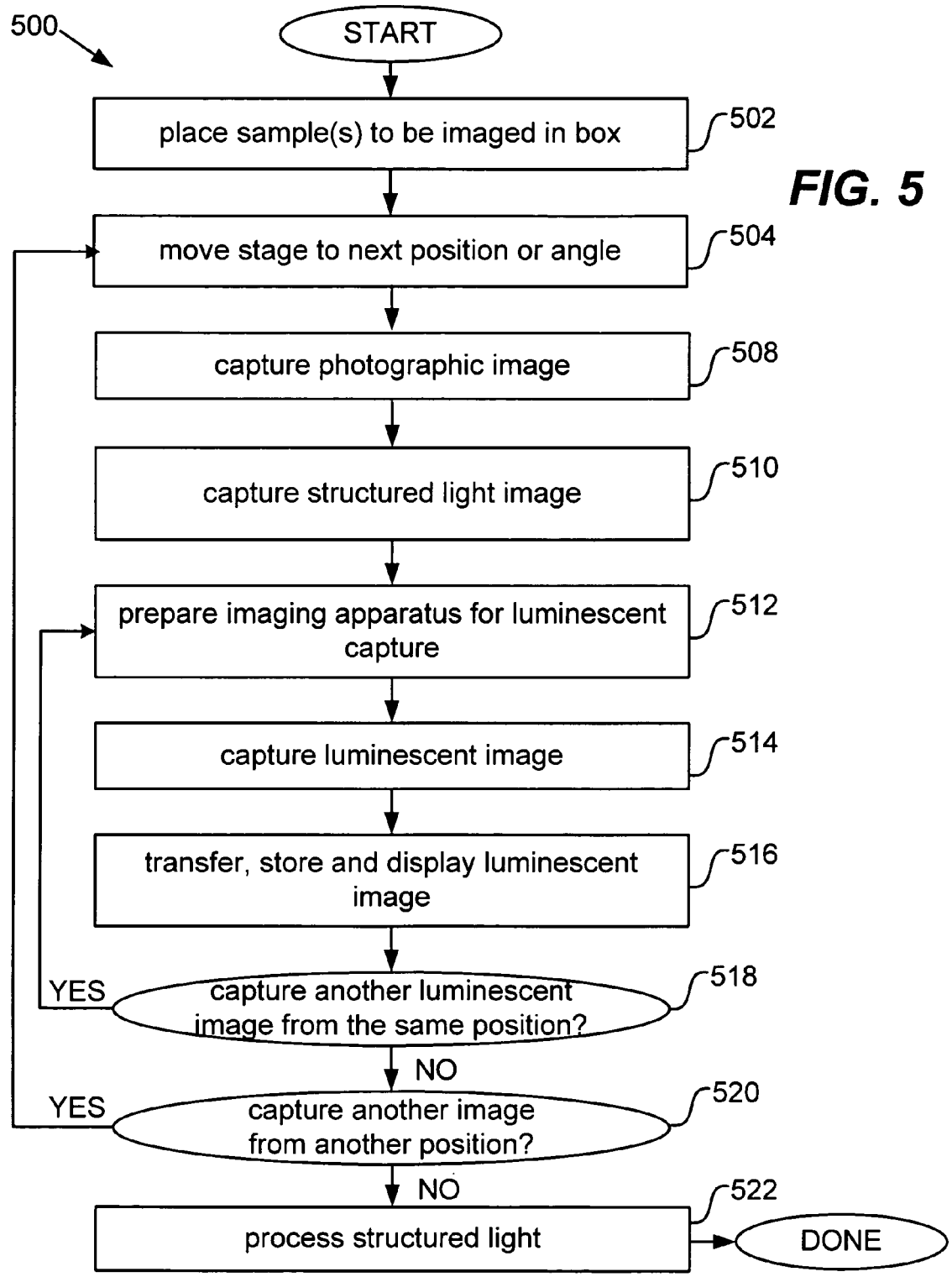
FIG. 5 illustrates a method of capturing photographic, structured light and luminescent images using an imaging system in accordance with one embodiment of the present invention.

Turning now to FIG. 5, process flow 500 illustrates a method of capturing photographic, structured light and luminescent images using the imaging system 10 in accordance with one embodiment of the present invention. Process flow 500 begins by placing an object such as an animal to be imaged for light emission on stage 204 within imaging box 12 (202). Using computer 28, a user inputs a desired position for stage 204. Based on the input, transport mechanism 202 moves stage 204 to the corresponding position according to a control signal provided by computer 28 (504). Light transmission device 111 also re-positions according to a control signal provided by computer 28.

The imaging box 12 and associated imaging components are then prepared for photographic image capture of the object. Preparation may include launching imaging and acquisition software (e.g., "LivingImage" as provided by Xenogen Corporation of Alameda, Calif.) on the computer 28 and initializing camera 20. Further preparations may include closing door 18, activating the photographic capture option in the software, focusing camera 20 to a specific depth of the object or animal, and turning on the lights in box 12. Preparations may also include focusing lens 100, selectively positioning an appropriate lens filter 118, setting the f-stop, etc. A photographic image is then captured (508). Upon completion of photographic capture, the photographic image data is transferred to an image processing unit 26 and/or a processor in computer system 28. These may be used to manipulate and store the photographic image data as well as process the data for display on computer monitor 38.

The imaging box 12 and associated imaging components are then prepared for structured light image capture of the object. Structured light preparations may include activating the structured light source, specifying structured light image capture parameters such as grid line density, etc. A structured light image is then captured (510). Upon completion of structured light capture, the structured light image data is transferred to an image processing unit 26 and/or a processor in computer system 28.

Subsequently, with stage 204 at the same position, the imaging apparatus 10 is prepared for luminescence image capture (512). Such preparation may include selecting luminescent exposure time and binning level using the computer 28, and turning off the lights in interior cavity 44. When ready, the CCD camera 20 then captures (514) the luminescence image over a set period of time (up to several minutes). The luminescence image data are transferred to the image processing unit 26 and/or a processor in computer 28 (516).

At this point, a user may manipulate and store the luminescence image data as well as process it for display on the computer display 38. The manipulation may also include overlaying the luminescent image with the photographic image and displaying the two images together as a 2-D "overlay" image, with the luminescence data typically shown in pseudocolor to show intensity. This overlay image may then be the basis for user analysis and may be analyzed and manipulated as desired. In particular, an analysis may include a summation of the illumination magnitudes over the pixels within a portion of the luminescence representation. Note that although the discussion will focus on a single luminescence representation for the overlay image, the process flow 500 may include taking multiple luminescence representations from the same position of stage 204, e.g., at the same time or a later time (518).

If desired, stage 204 may then be moved to a second position (520). While the stage is at the second position, one or more photographic and/or luminescence images of the object may be captured as described above. Upon completion of each image capture, a processor in computer 28 then receives the image data. Image collection may further continue by capturing images of the object from alternate positions and views of the sample.

As mentioned, the photon emission data may represent the specific pixels on the CCD camera 20 that detect photons over the duration of the image capture period. Together, a structured light photographic representation of the object and a luminescence representation of the object may be combined to form a structured light superposition or overlay image. Because the imaging apparatus 100 is typically used to measure the entire object 106, the data in the luminescence representation typically has one or more distinct luminescent portions of interest.

An image of the structured light is taken with camera 20. After the 2-D structured light images have been captured and stored, computer 28 may then process the structured light data to generate a surface topography (522). As one of skill in the art will appreciate, there are numerous conventional algorithms for reconstructing a surface from structured light images. For example, the phase shift of each line at all points on the image can be determined from a computationally-efficient 2D Fourier transform. The actual surface height is then computed by "unwrapping" the phase map.

Structured light capture and surface topology construction may be flexibly applied. In one embodiment, the present invention builds a surface topography of the animal for a surface that faces the camera only. In another embodiment, the present invention builds a surface topography of the animal for a large surface of the animal that is greater than just the surface facing the camera. In this case, imaging apparatus 10 captures a sequence of images from multiple positions. This sequence of images is taken at different viewing angles and provides the information necessary to stitch together multiple surface topography portions (see FIGS. 7A-7C).

The surface topography may then be used to reconstruct the location, brightness, and size of a light source within the animal. One suitable reconstruction algorithm (or inversion algorithm) suitable for use with the present invention is diffuse optical tomography. Diffuse optical tomography uses the 3D surface topology of the animal and to map the bioluminescent emission onto this 3D surface.

Processor 28 may apply any suitable reconstruction algorithm to the structured light information to obtain a 3D surface topography. As one of skill in the art will appreciate, there are numerous algorithms for reconstructing a surface from structured light images. For example, the phase shift of each line at all points on the image can be determined from a 2D Fourier transform. Such a process is described in detail in the article entitled "Fourier-transform method of fringe-pattern analysis for computer-based topography and interferometry," by M. Takeda, H. Ina and S. Kobayshi, JOSA 72, 156-160 (1982), which is incorporated herein by reference in its entirety. The actual surface height is then computed by "unwrapping" the phase map. Such a process is described in detail in the textbook entitled "Two-Dimensional Phase Unwrapping, Theory, Algorithms, and Software" by D. C. Ghiglia and M. D. Pritt, (John Wiley and Sons, New York, N.Y., 1998), which is incorporated herein by reference in its entirety.

Together, a structured light representation of the sample and a luminescence representation of the sample may be combined to form a structured light superposition or 3D overlay image, with the luminescence data typically shown in pseudocolor to visually characterize intensity.

Figure 6A:
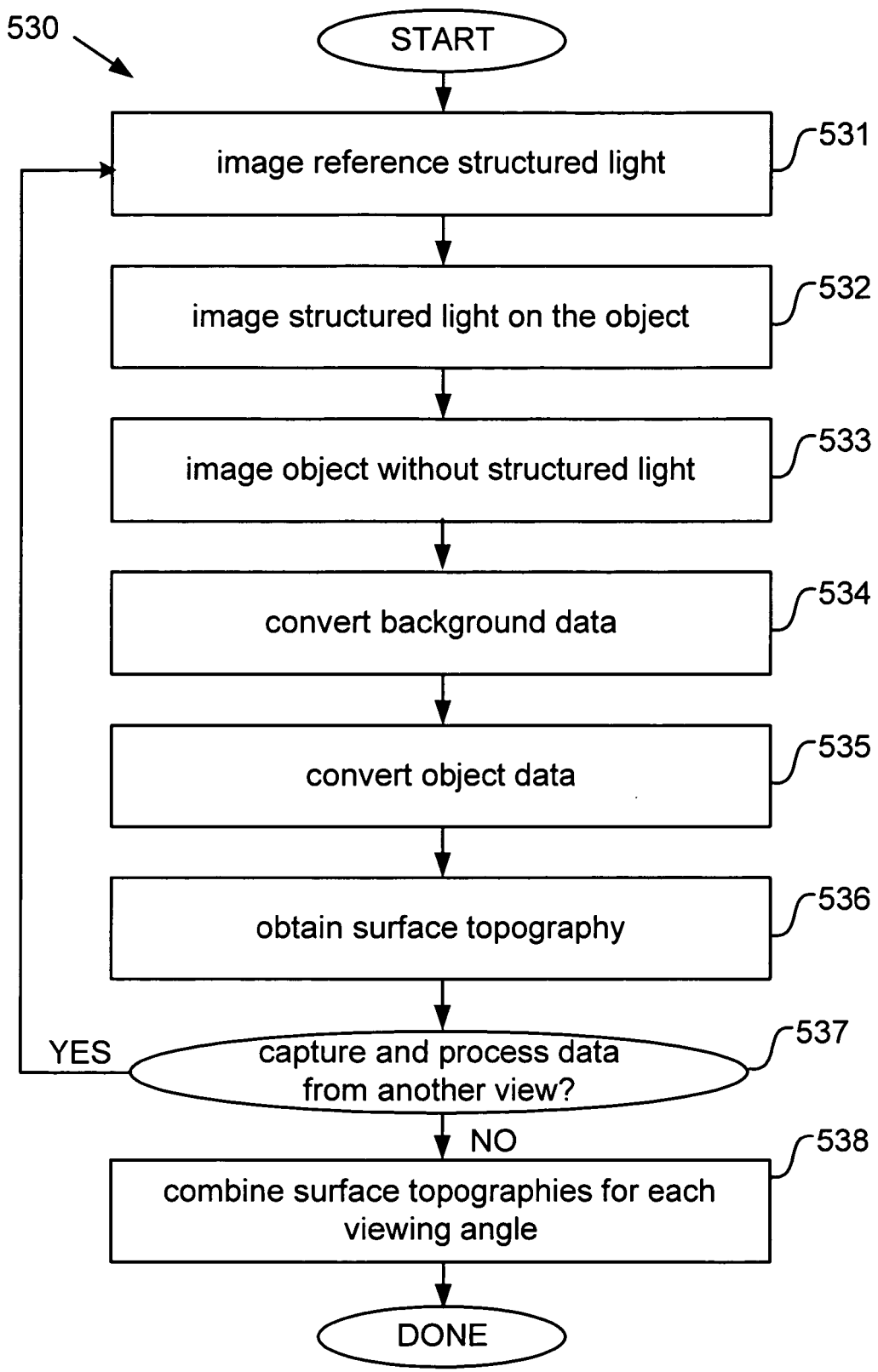
FIG. 6A illustrates a process flow for obtaining surface topography data in accordance with one embodiment of the present invention.
Figure 6H:
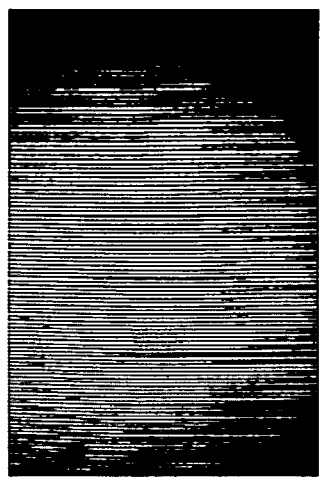
Figure 6H:
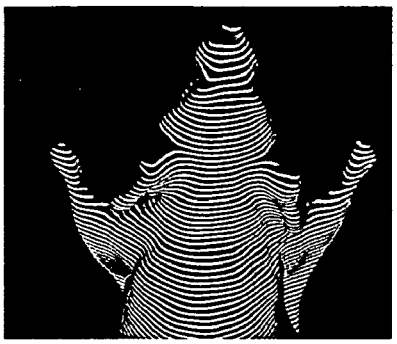
Figure 6H:
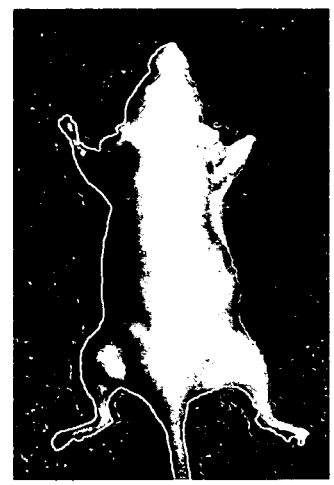
Figure 6H:
Figure 6H:
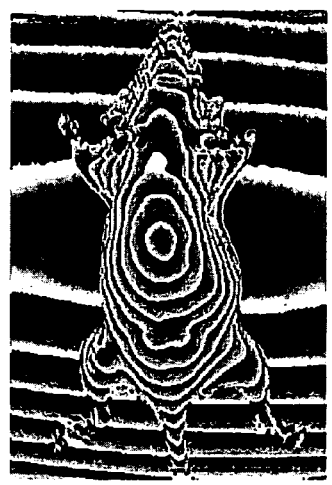
Figure 6H:
Figure 6H:

FIG. 6A illustrates a process flow 530 for using a light imaging system to obtain surface topography data in accordance with a specific embodiment of the present invention (502 from process flow 500). FIGS. 6B-6H illustrate pictorial representations of structured light imaging corresponding to process flow 530.

Process flow 530 begins by imaging a structured light reference to produce a pattern without the sample (531 and FIG. 6B). This may be performed by applying structured light to a stage or surface that the sample rests upon before the sample is imaged. During image capture of the sample, the stage is moved to common locations as those used in image capture without the sample.

Subsequently when the sample is in the imaging chamber, the sample is imaged with structured light (532 and FIG. 6C). Structured light uses a series of lines of light that are projected down on a sample at an angle to the surface normal. The lines bend as they pass over the sample, and the bend in the lines can be used to determine the height of the surface at all locations that are illuminated by a structured light projector. The projection angle is large enough to get sufficient "bend" in the lines to achieve spatial resolution, but small enough that large shadows are not present.

Process flow 530 then proceeds by imaging the sample without structured light (533 and FIG. 6D). The phase shift of each line at all points on the background and sample may be determined from a 2D Fourier transform.

The background data is then converted to a wrapped phase (534 and FIG. 6E). Here, the background data is Fourier transformed and filtered before a wrapped phase is calculated. Similarly, the sample data is converted to a wrapped phase (535 and FIG. 6F) by Fourier transforming and filtering the sample data, and the calculating a wrapped phase for the sample data.

Surface topography for the sample is then calculated (536 and FIG. 6G). In this case, this is performed by "unwrapping" the phase map. Several unwrapping algorithms are available to those of skill in the art for this task. For example, the phase shift of each line at all points on the image can be determined from using Fourier profilometry techniques. With these methods, a 2D Fast-Fourier transform (FFT) of the fringe data (FIG. 6D) is taken to determine the phase shift of the lines everywhere in the image (FIG. 6F). Since the phase will shift by many multiples of $2\pi$ for a typical object, the phase exhibits $2\pi$ jumps as seen in FIG. 6F. These phase jumps are "unwrapped" in order to determine the actual surface.

The above processes (531-536) may then be repeated (537) from different views and positions. Imaging a sample from multiple views provides additional information that helps techniques described herein provide a more accurate 3D surface rendering. The multiple images, or the partial surfaces obtained from each view in the 3D imaging system, are then registered together to form a complete 3D surface (538 and FIG. 6H). Registering can be accomplished by using non-linear least squares fitting techniques to minimize the distance between mesh elements on two surfaces that are to be connected. Typically, the surfaces should have a starting orientation that is fairly close to the final registered position. In other words, only fine adjustments to the surface positions may be accommodated with this method. Another registration technique is to provide an absolute reference line or fiducial of some kind in the image, which gives the absolute position of any partial surface with respect to the stage, for example. If the absolute positioning of each surface is accurate enough, then the non-linear fitting method described above can be skipped.

The surface topography derived from structured light data has many uses. Some users may employ the surface topography to provide a pictorial view of the object surface. The surface topography may also be used in tomographic reconstruction of an internal light source. In this case, using a) one or more luminescent images that relate to a light source internal to the object and b) the orientation of the surface topography or a surface mesh built with the surface topography, photon density just below the surface can be determined. The photon density just below the surface is related to the light intensity emitted from the surface and captured in the luminescent images. A set of volume elements can be constructed in the volume interior to the surface. The source strength in each volume element may then be determined using the photon density just below the surface. Further description of one suitable system for tomographic reconstruction is described in commonly owned pending patent application Ser. No. 10/606,976 and entitled "Method and Apparatus for 3D Imaging of Internal Light Sources", which was incorporated by reference above.

Thus, the processing hardware and software may also be applied to perform tomographic reconstruction and various image processing functions described herein. For example, the processor may be configured to produce a 3D structured light representation using structured light information included in images taken from one or more positions of the stage in the interior cavity. In one embodiment, imaging system 10 employs a quantitative model that estimates the diffusion of photons in tissue. In one embodiment, the model processes in vivo image data and in order to spatially resolve a 3D representation of the size, shape, and location of the light emitting source. Typically, a tomographic model is stored as instructions in memory of processing system 28. Various diffusion and reconstruction models may be implemented by system 10 to represent photon propagation through a mammalian subject or a phantom device described herein. One suitable tomographic example of software that builds a digital representation of a light source internal to a mammalian sample or phantom device using data from one or more images is described in commonly owned and pending patent application Ser. No. 10/606,976 entitled "Method and Apparatus for 3D Imaging of Internal Light Sources" and naming Brad Rice et al. as inventors. This application is incorporated by reference herein and its entirety for all purposes.

Although structured light generation has been described with respect to structured light sources and methods described above, the present invention also relates to machine-readable media that include program instructions, state information, etc. for performing structured light operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). A processor as described above may then be configured to run from the stored instructions and perform many of the methods described above (e.g., process flow 530). Examples of program instructions include both machine code, such as produced by a compiler, and files containing higher level code that may be executed by the computer using an interpreter.

3D Imaging Apparatus with Structured Light

Figure 7A:
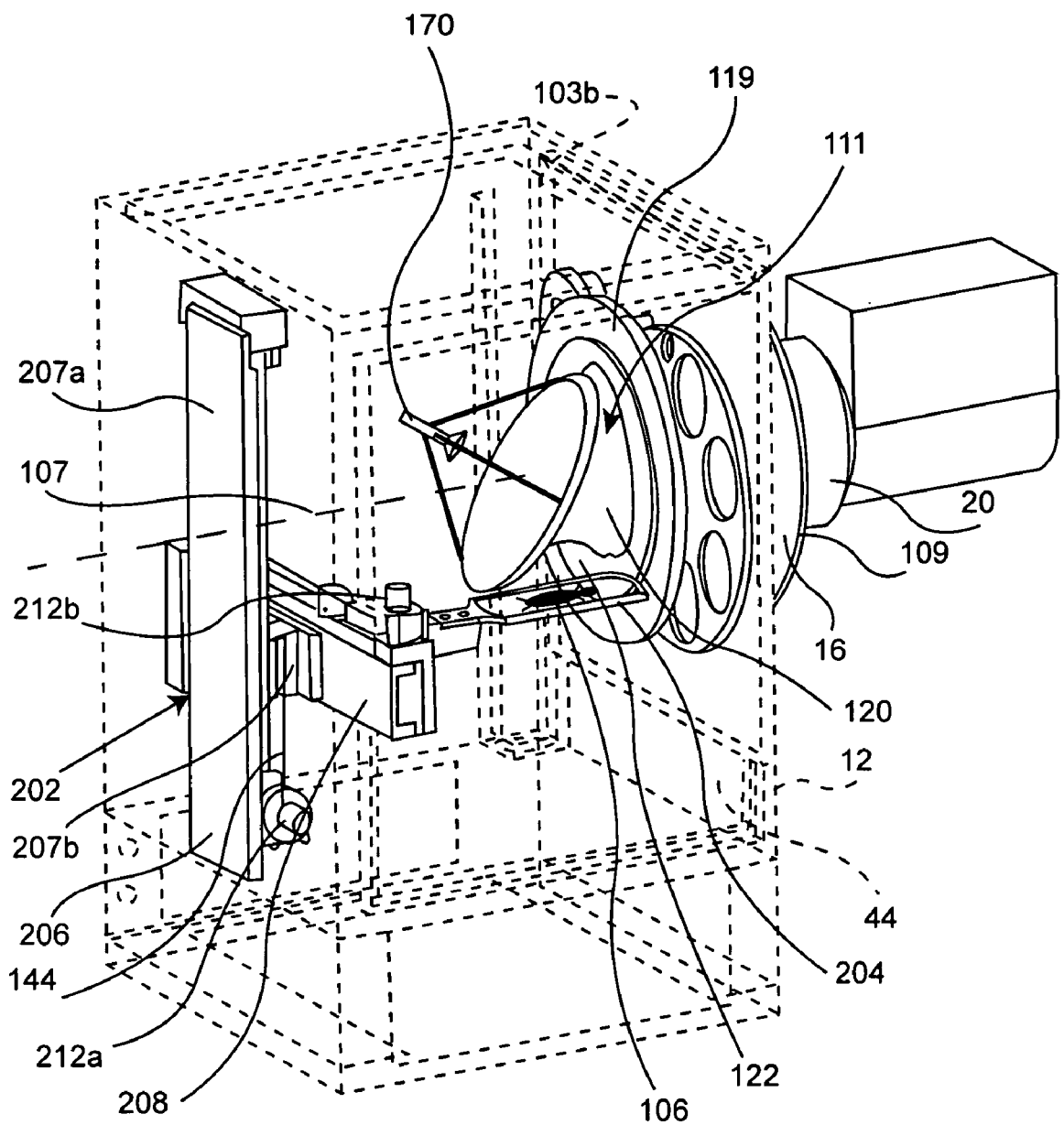
FIG. 7A illustrates a top perspective view of components in an imaging box with the exterior walls removed showing the moveable stage directly below a fixed datum in accordance with one embodiment of the present invention.
Figure 7B:
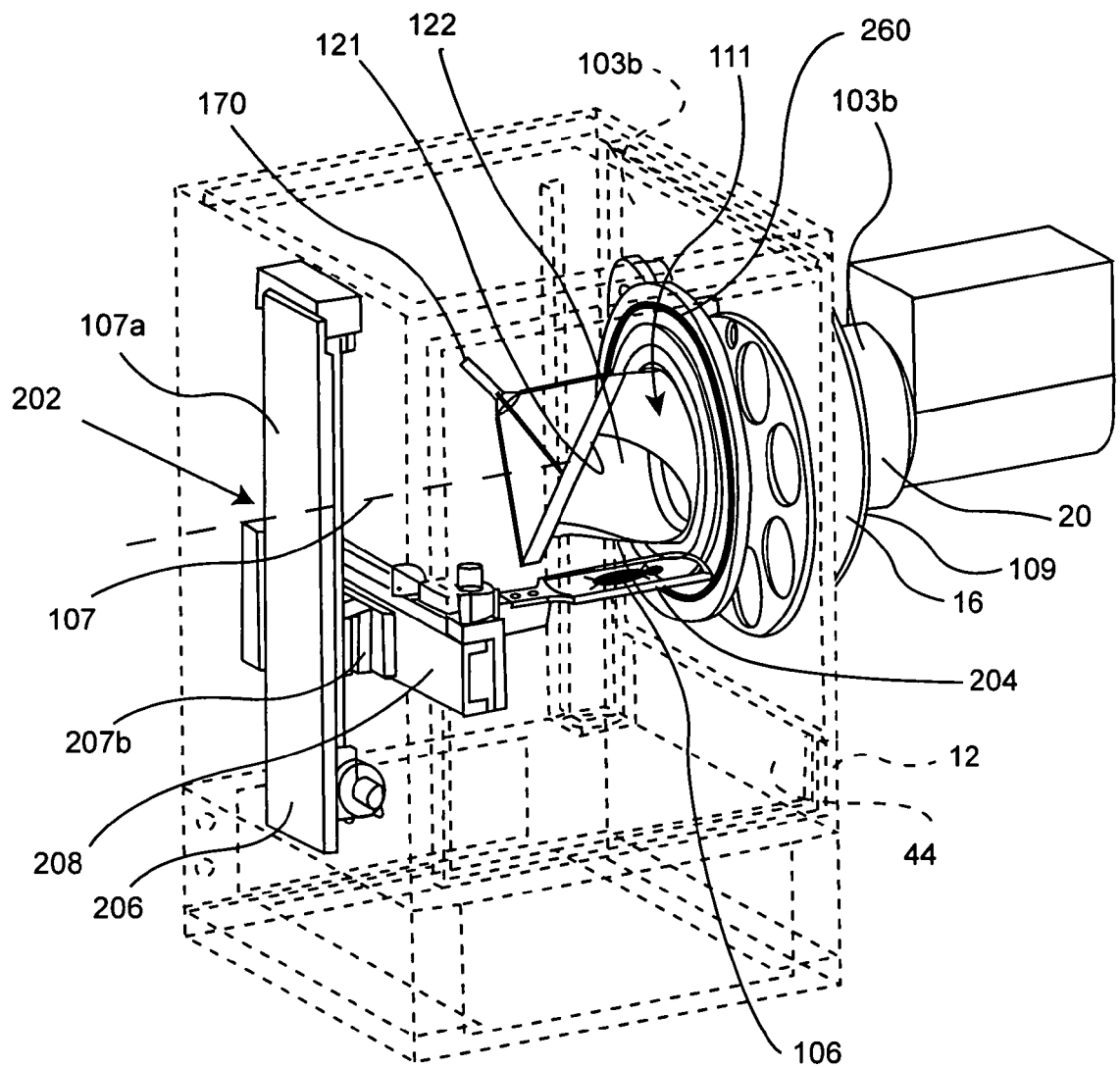
FIG. 7B illustrates a top perspective view of the components in an imaging box with the exterior walls removed showing the moveable stage below and off-center from the fixed datum in accordance with one embodiment of the present invention.
Figure 7C:
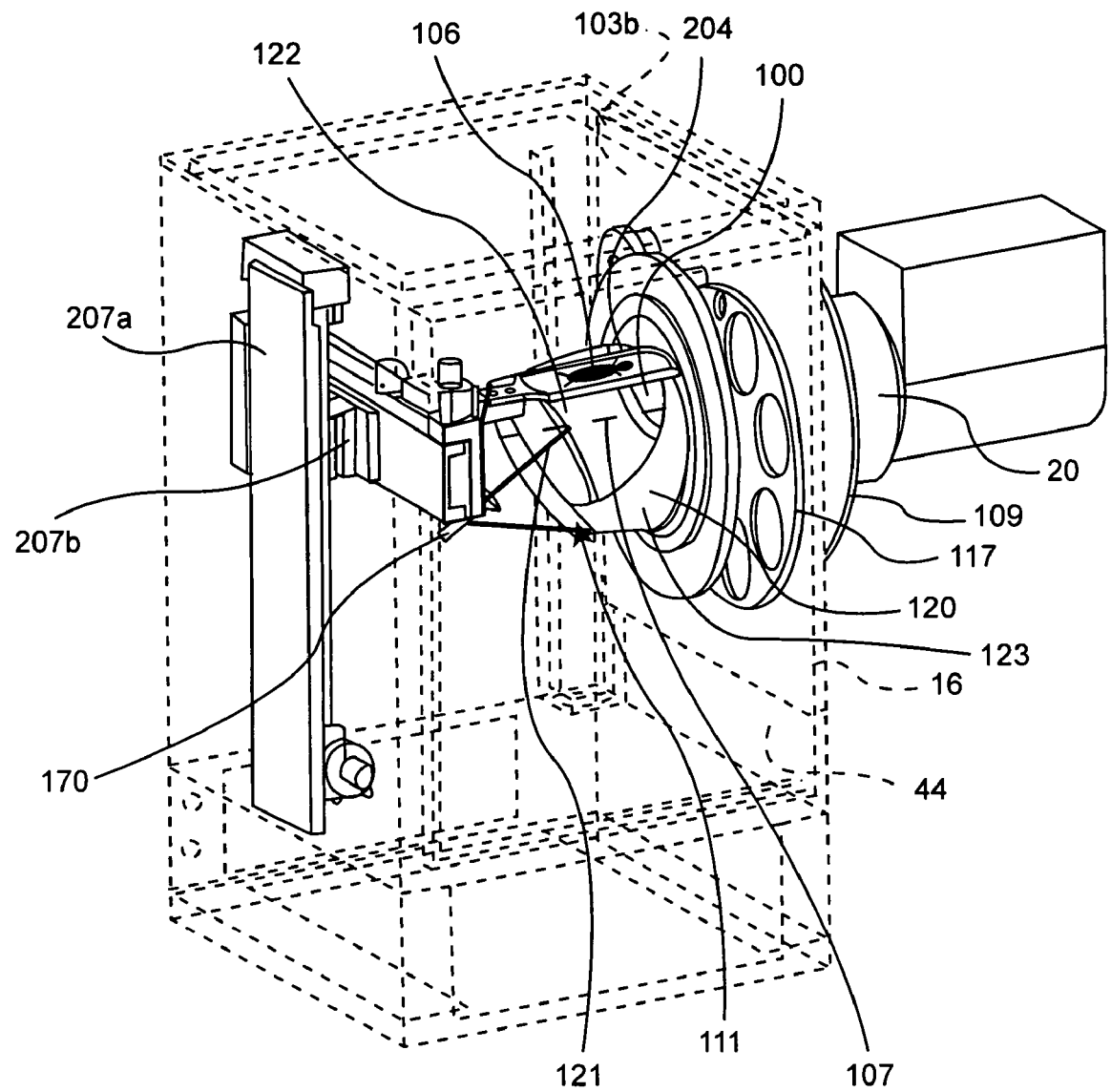
FIG. 7C illustrates a top perspective view of the components in an imaging box with the exterior walls removed showing the moveable stage above and off center from the fixed datum in accordance with one embodiment of the present invention.

In one embodiment, the present invention builds a surface topography of the animal for a large surface of the animal that is greater than just the surface facing the camera. In this case, imaging apparatus 10 captures a sequence of images from multiple positions. This sequence of images is taken at different viewing angles and provides the information necessary to stitch together multiple surface topography portions. Each structured light image provides the surface topology for approximately the facing half of the animal only. By taking images from several viewing angles, e.g., about every 45 degrees, the entire 3D surface of the animal can be reconstructed by "stitching" together the partial surface reconstructions obtained from each view. FIGS. 7A-C illustrate one system suitable for obtaining a sequence of structured light images from multiple viewing angles.

FIG. 7A is a top perspective view of internal components in an imaging box with the exterior walls removed showing stage 204 directly below a fixed datum 107. FIG. 7B is a top perspective view of the components in box 12 with the exterior walls removed showing stage 204 below and off-center from fixed datum 107. FIG. 7C is a top perspective view of the components in box 12 with the exterior walls removed showing stage 204 above and off center from fixed datum 107.

As shown in FIG. 7C, a camera mount 109 is attached to side housing 16 of side wall 103b. Camera mount 109 is adapted to receive and position camera 20 relative to fixed datum 107 for viewing of object 106 within cavity 44 by camera 20. While camera 20 is capable of capturing photographic and structured light images, it is also sensitive enough to capture luminescence images thereof.

A moveable stage apparatus 200 is disposed in interior cavity 44, and includes a transport mechanism 202 and a stage 204 to support the light-emitting object 106. Moveable stage apparatus 200 is capable of two degrees of freedom movement to reposition the stage 204 (and object 106) to a plurality of positions within interior cavity 44. Any one position therebetween may be retained for image capture.

As shown in FIGS. 7A-C, the transport mechanism 202 in the embodiment comprises two linear actuators 206 and 208 oriented at substantially perpendicular to one another. Each linear actuator 206 and 208 is capable of positioning stage 204 linearly along the respective actuator. Linear actuator 206 provides vertical positioning for stage 204 while linear actuator 208 provides horizontal positioning for stage 204. Linear actuator 206 has a stationary portion attached to box 12 and a mobile portion attached to linear actuator 208. Linear actuator 208 has a relatively stationary portion attached to linear actuator 206 and a mobile portion attached to stage 204. An example of one such linear actuator suitable for use in the transport mechanism 202 is a LC-33 produced by Thomson Industries of Port Washington, N.Y.

The transport mechanism 202 preferably includes a set of position sensors that are operably coupled to the computer 28 to provide position feedback to control the position of stage 204. Linear actuators 206 and 208, position sensors 212, and computer 28 combine to provide closed loop position control for stage 204 within interior cavity 44. More specifically, a user, via computer 28, may input one or more positions for stage 204 along a substantially circular path about fixed datum 107. In one embodiment, a user provides a viewing angle for stage 204 relative to fixed datum 107. Software included in computer 28 then converts the viewing angle into control signals for moving each of the linear actuators 206 and 208.

Light transmission device 111 directs light reflected or emitted from object 106 along the direction of fixed datum 107 and into lens 100 for image capture by camera 20. Light transmission device 111 is mounted to housing 16 using stationary bracket 119 (FIG. 7A), which includes circumferentially disposed bearings between stationary bracket 119 and moving bracket 126 that allow turning mirror assembly 120 to rotate freely relative to stationary bracket 119. Mirror assembly 120 is thus rotably coupled to housing 16 and rotates about an axis co-axially aligned with the stationary axis of the fixed datum 107.

Referring to FIG. 7C, mirror assembly 120 comprises an angled mirror 121 that reflects light from object 106 on stage 204 in a direction along fixed datum 107. Outer wall 123 is substantially cylindrical and includes aperture 122 that enables light to pass between stage 204 and turning mirror 121. Outer wall 123 of mirror assembly 120 also prevents residual light in interior cavity 44 not directly associated with the current viewing angle of stage 204 from reaching lens 100. This is partially performed by configuring mirror 121 to be sufficiently long to span the length of stage 204. As the stage is positioned along the circular path about the stationary axis, outer wall 123 and turning mirror 121 cooperate to collect light primarily from the angular direction of stage 204 which is then reflected along fixed datum 107 for reception by lens 100.

Figure 7D:
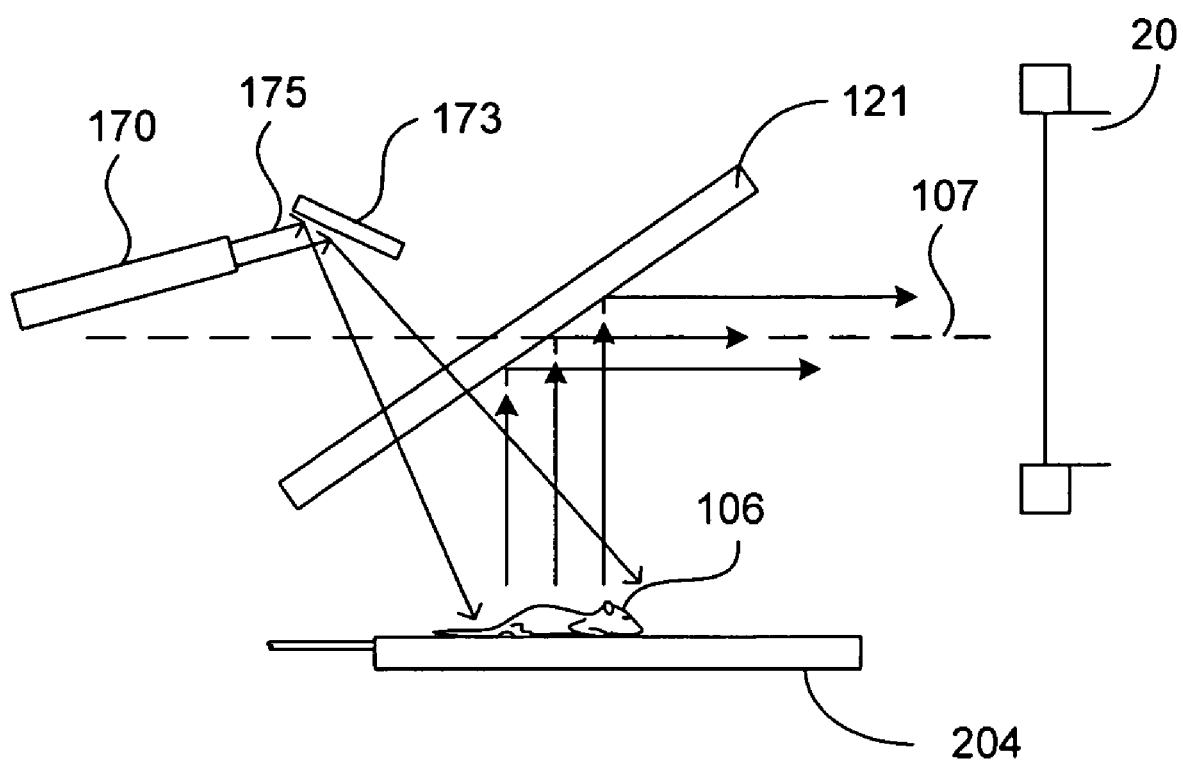
FIG. 7D illustrates a simplified view of light transmission within an imaging box using the light transmission device of FIG. 7A.

FIG. 7D illustrates a simplified view of light transmission within box 12 using light transmission device 111. FIG. 7D also show another configuration for a structured light projector 170. As shown, structured light 175, emitted from structured light projector 170, reflects off a mirror 173, passes through partially transparent mirror 121, and onto object 106. In one embodiment, the partial transparence of mirror 121 is achieved using a half-silvered or partially silvered mirror. In another embodiment, a dichroic mirror having wavelength specific transparency properties is used. The structured light 175 may then be captured by camera 20.

The two degrees of freedom movement provided by transport mechanism 202 allow stage 204 and object 106 to be positioned at multiple angles relative to fixed datum 107 for image capture by camera 20. Thus, based on user input via computer 28, transport mechanism 202 and light transmission device 111 cooperate to direct light from object 106 on stage 204 to fixed datum 107 and lens 100 to capture image using camera 20. In addition to providing full 360 degree angular viewing of object 106 about the circular path, transport mechanism 202 is capable of varying the image depth for a given angle of stage 204 relative to fixed datum 107. Together, transport mechanism 202 and light transmission device 111 cooperate to provide a field of view for camera 20 in the range of about 7.5 cm to about 16.5 cm. In a specific embodiment, light transmission device 111 cooperate to provide a field of view for camera 20 in the range of about 13 cm to about 16.5 cm. Similar to the user initiated angular position control described above, a user may input a desired focal depth and viewing angle for stage 204. Software included in computer 28 and linear actuators 206 and 208 would then combine to position stage 204 at the desired angle and depth relative to fixed datum 107.

Stage

As the term is used herein, a stage refers to a structure used to support an object during image capture. Flat surfaces are well suited for use, such as a fixed flat bottom panel in the imaging box (a stationary stage). In another embodiment, the stage is moveable. One suitable vertical positionable stage was discussed above. In general, the present invention is not limited to any particular stage structure or configuration.

Some stages may include transparent portions to permit image capture through the stage. For example, the transport mechanism 202 described above relies on some transparency in the stage.

Figure 8A:
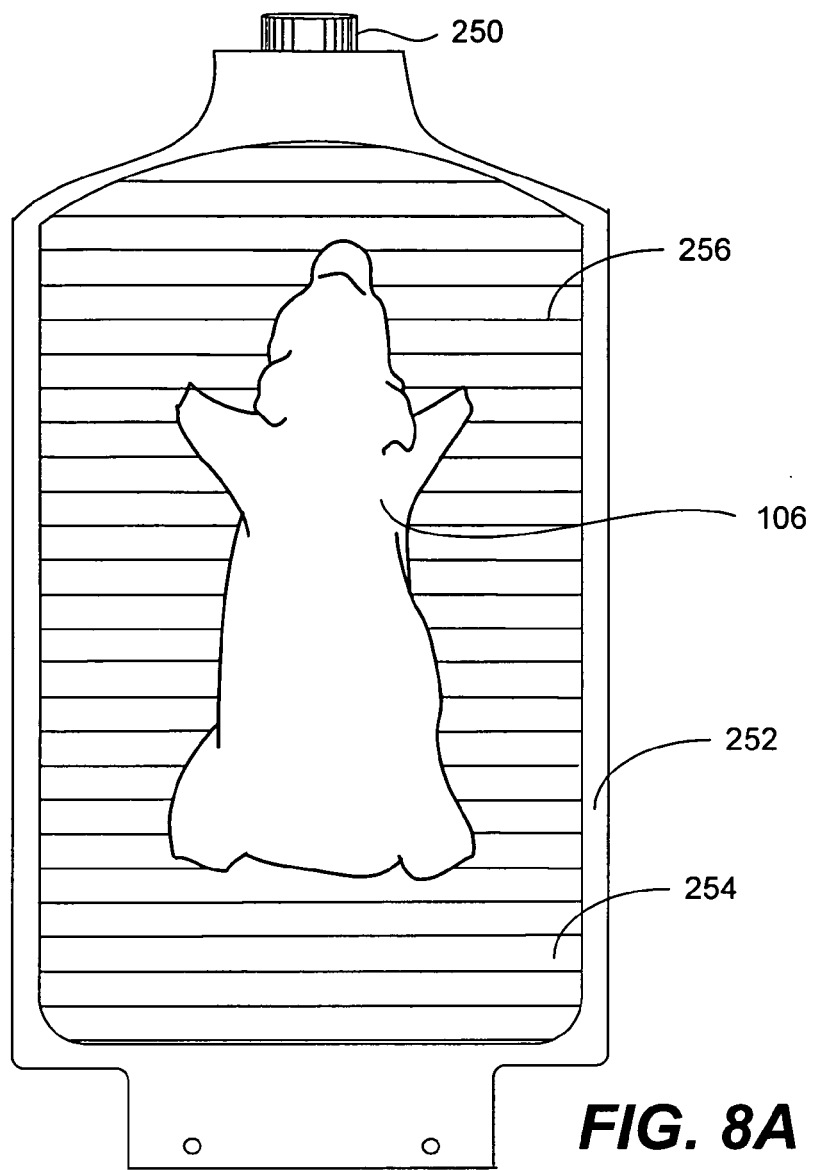
FIGS. 8A and 8B illustrate a top and side view, respectively, of a stage included in an imaging box in accordance with one embodiment of the present invention.
Figure 8B:
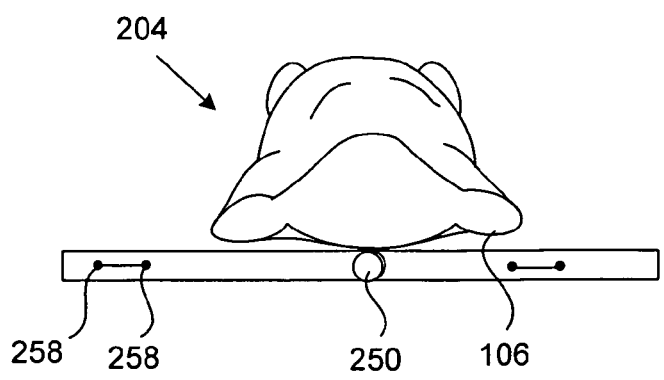

Referring now to FIGS. 8A and 8B, stage 204 comprises a frame 252 and a transparent portion 254. Transparent portion 254 allows light emitted or reflected from object 106 to be transmitted therethrough with substantially no interference and minimal distortion for any position of stage 204 about fixed datum 107. Transparent portion 254 preferably, comprises a transparent wire array 256 that supports object 106. In a specific embodiment, transparent wire array 256 is a single transparent nylon line interwoven through holes 258 on opposing edges of frame 252 and secured in a taut manner to support object 106. In another embodiment, array 256 is a mesh that resembles a cross pattern grid similar to a tennis racket mesh.

In a specific embodiment, stage 204 includes hardware based crash protection measures that prevent undesirable contact between stage 204 and other components within box 12. In a specific embodiment, crash pin 250 is placed on the side of stage 204 closest to the camera 20, as shown in FIG. 8A. Crash pin 250 prevents contact between stage 204 and components within cavity 44. To prevent contact between stage 204 and light transmission device 111, camera 20 or wall 103b, a metal ring 260 is perimetrically disposed around light transmission device 111 on stationary bracket 119.

Although various details have been omitted for brevity's sake, obvious design alternatives may be implemented. For example, although the present invention has been discussed primarily in the context of a structured light source useful for in-vivo imaging applications, the present invention is suitable for other imaging applications and may be tailored correspondingly. Therefore, the present examples are to be considered as illustrative and not restrictive, and the invention is not to be limited to the details given herein, but may be modified within the scope of the appended claims.

What is claimed is:

1. An imaging system for providing a three-dimensional surface representation of an animal, the imaging system comprising:
    a camera;
    a structured light source configured to produce structured light for transmission onto the animal, wherein interception of the structured light by the animal generates structured light surface information for the animal;
    a processor configured to a) produce a three-dimensional surface representation of at least a portion of the animal using the structured light surface information obtained by the camera, and b) use the three-dimensional surface representation of at least the portion of the animal to reconstruct a location, brightness, or size of a light source within the animal.

2. The system of claim 1 wherein the processor is configured to produce the three-dimensional surface representation of the animal using instructions stored in memory that determine how to produce the three-dimensional surface representation from the structured light surface information.

3. The system of claim 1 wherein the processor is further configured to map the location, brightness, or size of the light source onto the three-dimensional surface representation.

4. The system of claim 1 wherein the processor is further configured to provide a superposition of the three-dimensional surface representation with the location, brightness, or size of the light source within the animal.

5. The system of claim 1 wherein the processor is further configured to employ a quantitative model that estimates the diffusion of photons from the light source in tissue of the animal.

6. The system of claim 1 wherein the three-dimensional surface representation includes a surface mesh.

7. The system of claim 6 wherein the processor is further configured to relate i) photon density just below an animal surface to ii) light intensity emitted from the three-dimensional surface representation and captured in a luminescent image by the camera.

8. The system of claim 1 wherein the structured light source comprises a structured light projector configured to produce the structured light.

9. The system of claim 1 further comprising a light transport device that transmits structured light from a surface of the animal to the camera.

10. The system of claim 6 wherein the structured light source is coupled to the light transport device.

11. The system of claim 7 wherein the light transport device comprises a mirror configured to intercept light emitted from the animal before receipt by the camera.

12. The system of claim 1 wherein the structured light source comprises a scanning laser galvanometer that includes:
a laser that produces a beam of light; and
at least one mirror positionable to reflect the beam of light and cast a grid of lines onto the animal.

13. The system of claim 1 wherein the processor is configured to reconstruct the location, brightness, or size of the light source within the animal using instructions stored in memory that determine how to reconstruct the location, brightness, or size of the light source using the thee-dimensional surface representation of at least the portion of the animal.

14. An imaging system for providing a three-dimensional surface representation of an animal, the imaging system comprising:
a camera;
a structured light source configured to produce structured light for transmission onto the animal, wherein interception of the structured light by the animal generates structured light surface information for the animal;
a processor configured to a) produce a three-dimensional surface representation of at least a portion of the animal using the structured light surface information obtained by the camera, and b) use the three-dimensional surface representation of at least the portion of the animal to reconstruct a location of a light source within the animal.

15. The system of claim 14 wherein the processor is configured to produce the three-dimensional surface representation of the animal using instructions stored in memory that determine how to produce the three-dimensional surface representation from the structured light surface information.

16. The system of claim 14 wherein the processor is configured to reconstruct the location, brightness, or size of the light source within the animal using instructions stored in memory that determine how to reconstruct the location, brightness, or size of the light source using the three-dimensional surface representation of at least the portion of the animal.

17. The system of claim 14 wherein the processor is further configured to map the location, brightness, or size of the light source onto the three-dimensional surface representation.

18. The system of claim 14 wherein the processor is further configured to provide a superposition of the three-dimensional surface representation with the location, brightness, or size of the light source within the animal.

19. The system of claim 14 wherein the processor is further configured to employ a quantitative model that estimates the diffusion of photons from the light source in tissue of the animal.

20. The system of claim 14 wherein the three-dimensional surface representation includes a surface mesh.

21. The system of claim 20 wherein the processor is further configured to relate i) photon density just below an animal surface to ii) light intensity emitted from the three-dimensional surface representation and captured in a luminescent image by the camera.

22. The system of claim 14 wherein the structured light source comprises a structured light projector configured to produce the structured light.

23. The system of claim 14 further comprising a light transport device that transmits structured light from a surface of the animal to the camera.

24. The system of claim 23 wherein the structured light source is coupled to the light transport device.

25. The system of claim 24 wherein the light transport device comprises a minor configured to intercept light emitted from the animal before receipt by the camera.

26. The system of claim 14 wherein the structured light source comprises a scanning laser galvanometer that includes:
a laser that produces a beam of light; and
at least one minor positionable to reflect the beam of light and cast a grid of lines onto the animal.

* * * * *